United States Patent
Puetz et al.

(10) Patent No.: US 7,358,235 B2
(45) Date of Patent: Apr. 15, 2008

(54) ANALOGS OF NITROBENZYLTHIOINOSINE

(75) Inventors: Claudia Puetz, Dueren (DE); Corinna Sundermann, Aachen (DE); Bernd Sundermann, Aachen (DE); Adriaan Pieter Ijzerman, Haarlem (NL); Reynier Tromp, Leiden (NL); Jacobien Von Frijtag Drabbe Kuenzel, Haarlem (NL)

(73) Assignees: Gruenenthal GmbH, Aachen (DE), part interest; Leiden University, EZ Leiden (NL), part interest ( * ) Notice: Subject to any disclaimer, the term of this patent is extended or adjusted under 35 U.S.C. 154(b) by 405 days.

(21) Appl. No.: 10/958,681

(22) Filed: Oct. 6, 2004

(65) Prior Publication Data

US 2005/0096293 A1    May 5, 2005

Related U.S. Application Data

(63) Continuation of application No. PCT/EP03/03724, filed on Apr. 10, 2003.

(30) Foreign Application Priority Data

Apr. 10, 2002   (EP)   ................... 02076420

(51) Int. Cl.
- *C07D 473/38* (2006.01)
- *C07D 471/04* (2006.01)
- *C07D 473/20* (2006.01)
- *A61K 31/52* (2006.01)
- *A61P 25/04* (2006.01)

(52) U.S. Cl. .............. 514/45; 544/265; 544/268; 514/263.2; 514/263.21; 514/263.22; 514/263.24; 536/27.21; 536/27.22; 536/27.23; 536/27.8; 546/118

(58) Field of Classification Search ............ 514/263.2, 514/263.21, 263.22, 263.24, 45; 544/265, 544/268; 536/27.21, 27.22, 27.23, 27.8
See application file for complete search history.

(56) References Cited

U.S. PATENT DOCUMENTS

| | | | |
|---|---|---|---|
| 3,948,886 A | | 4/1976 | Shuman et al. |
| 5,017,701 A | * | 5/1991 | Grinter et al. ............ 544/276 |
| 5,780,450 A | | 7/1998 | Shade et al. |
| 5,965,563 A | * | 10/1999 | Buzzetti et al. .......... 514/263.2 |
| 2003/0187261 A1 | * | 10/2003 | Havlicek et al. ............ 544/276 |

FOREIGN PATENT DOCUMENTS

| | | |
|---|---|---|
| DE | 25 24 284 | 10/1976 |
| EP | 421819 | 4/1991 |
| WO | WO 89 11274 | 11/1989 |
| WO | WO 93 14103 | 7/1993 |
| WO | 96 40165 | 12/1996 |
| WO | WO 97 30713 | 8/1997 |
| WO | WO 9945935 | 9/1999 |

OTHER PUBLICATIONS

Braajeswar, P., "Inhibitors of Nucleoside Transport. A Structure-Activity Study Using Human Erythrocytes", Journal of Medicinal Chemistry 1975, vol. 18, No. 19.

* cited by examiner

*Primary Examiner*—Mark L. Berch
(74) *Attorney, Agent, or Firm*—Crowell & Moring LLP

(57) ABSTRACT

Analogs or derivatives of nitrobenzylthioinosine compounds. The use of these new analogs of nitrobenzylthioinosine and methods for the treatment of pain and various other indications using these analogs of nitrobenzylthioinosine as well as pharmaceutical compositions including analogs of nitrobenzylthioinosine.

17 Claims, No Drawings

ANALOGS OF NITROBENZYLTHIOINOSINE

CROSS REFERENCE TO RELATED APPLICATIONS

This application is a continuation of international patent application no. PCT/EP03/03724, filed Apr. 10, 2003, designating the United States of America, and published in English as WO 03/084975 A1, the entire disclosure of which is incorporated herein by reference. Priority is claimed based on European patent application no. 02076420.5, filed Apr. 10, 2002.

FIELD OF THE INVENTION

This invention relates to new analogs or derivatives of nitrobenzylthioinosine, the use of these new analogs of nitrobenzylthioinosine in methods of treating of pain and various other diseases as well as pharmaceuticals comprising at least one new analog of nitrobenzylthioinosine.

BACKGROUND OF THE INVENTION

The treatment of pain conditions is of great importance in medicine. There is currently a world-wide need for additional pain therapy. The pressing requirement for a target-oriented treatment of pain conditions which is right for the patient, which is to be understood as the successful and satisfactory treatment of pain for the patients, is documented in the large number of scientific works which have recently and over the years appeared in the field of applied analgesics or on basic research on nociception.

The facilitated, carrier-mediated transport of nucleosides across mammalian cell

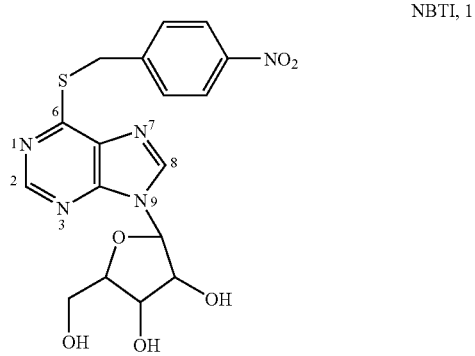

NBTI, 1 membranes can be inhibited by a number of ligands including nucleoside derivatives such as nitrobenzylthioinosine (NBTI, 1) (Plagemann, P. G. W.; Wohlhueter, R. M.; Woffendin, C. Biochim Biophys Acta 1988, 947, 405-443), and non-nucleoside compounds including marketed substances such as dipyridamole and dilazep. (Thom, J. A.; Jarvis, S. M. Gen. Pharmac. 1996, 27, 613-620; I Jzerman, A. P.; Voorschuur, A. H. Naunyn-Schmiedeberg's Arch Pharmacol 1990, 342, 336-341 (and refs therein)). Such compounds contribute to the physiological actions of adenosine. Through their blockade of the transport protein they increase the extracellular concentration of adenosine. This increase in adenosine levels causes a more profound occupancy of adenosine receptors through which adenosine exerts many of its physiological effects. The high hydrophilicity of NBTI and other transport inhibitors, however, may hinder their penetration into the CNS, where adenosine is involved in e.g., counteracting neuropathic pain.

An earlier study indicated that a nitro group preferably at the 4-position of the benzyl moiety in NBTI is a prime factor in determining the potency of inhibition of nucleoside transport in human erythrocytes. (Paul, B.; Chen, M. F.; Paterson, A. R. P. J. Med. Chem. 1975, 18, 968-973; Baldwin, S. A.; Mackey, J. R.; Cass, C. E.; Young, J. D. Molecular Medicine Today 1999, 5, 216-224). To gain further information on the interaction of NBTI with the nucleoside transporter-associated binding site we systematically replaced a number of substituents at C6 and N9. Also the 1-deaza-2-chloro analog of NBTI was prepared. A primary aim was to provide substances with reduced polarity while maintaining substantial affinity for the transport protein.

SUMMARY OF THE INVENTION

One object of certain embodiments of the present invention is to find a substance useful in the treatment of pain as well as also other indications. Another object of certain embodiments is to develop pharmaceutical compositions for these treatments and related treatment methods.

It has now been found that the inventive derivatives of nitrobenzylthioinosine are surprisingly useful in the treatment of pain and other indications.

In certain embodiments, the invention relates to a derivative of nitrobenzylthioinosine according to formula I,

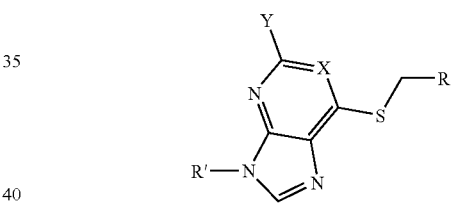

I wherein

X is selected from C or N;

Y is selected from H, OH, SH, F, Cl, Br, I, —CF$_3$, —CHF$_2$, —CH$_2$F, —OCH$_3$, —OC$_2$H$_5$, —CH$_3$, —C$_2$H$_5$;

R is selected from phenyl, benzyl, heteroaryl, or phenyl condensed with a heteroaryl, mono-or multisubstituted or unsubstituted respectively;

R' is selected from ribose, mono-or multisubstituted or unsubstituted; C$_{1-6}$-alkyl saturated or unsaturated, mono-or multisubstituted or unsubstituted; C$_{3-8}$-cycloalkyl or C$_{3-8}$-cycloalkyl containing 1 or 2 heteroatoms selected from S, O or N in the ring, mono-or multisubstituted or unsubstituted respectively; phenyl or benzyl, mono-or multisubstituted or unsubstituted respectively; or C$_{1-6}$-alkyl-O—R" with alkyl saturated or unsaturated, mono-or multisubstituted or unsubstituted and R" selected from phenyl, heteroaryl, C$_{3-8}$-cycloalkyl or C$_{3-8}$-cycloalkyl containing 1 or 2 heteroatoms selected from S, O or N in the ring, mono-or multisubstituted or unsubstituted respectively;

optionally in the form of its racemate, pure stereoisomers, especially enantiomers or diastereomers or in the form of mixtures of stereoisomers, especially enantiomers or diastereomers, in any suitable ratio;

in the form illustrated or in form of the acid or base or in form of a salt, especially a physiologically acceptable salt, or in form of a solvate, especially a hydrate.

These derivatives of nitrobenzylthioinosine are surprisingly effective in the treatment of pain and in other indications. Inhibitors of nucleoside transport have a potential as drugs enhancing adenosine's actions in the CNS. As such, they may be used in the treatment of chronic and/or neuropathic pain, epilepsy and other CNS-related disorders. Currently available ligands are often very hydrophilic, preventing substantial passage of the blood-brain barrier. The compounds according to the invention show decreased hydrophilicity. Many compounds proved to have affinities in the nanomolar range with a substantial reduction in polarity achieved. These compounds are promising to have more favorable characteristics, especially in terms of absorption and distribution.

In the sense of this invention alkyl- or cycloalkyl means saturated or unsaturated (but not aromatic), branched, unbranched and cyclic hydrocarbons that are unsubstituted monosubstituted or multisubstituted. $C_{1-2}$-alkyl denominates C1- or C2-alkyl; $C_{1-3}$-alkyl C1-, C2- or C3-alkyl; $C_{1-4}$-alkyl C1-, C2-, C3- or C4-alkyl; $C_{1-5}$-alkyl C1-, C2-, C3-, C4- or C5-alkyl; $C_{1-6}$-alkyl C1-, C2-, C3-, C4-, C5- or C6-alkyl; $C_{1-7}$-alkyl C1-, C2-, C3-, C4-, C5-, C6- or C7-alkyl; $C_{1-8}$-alkyl C1-, C2-, C3-, C4-, C5-, C6-, C7- or C8-alkyl; $C_{1-10}$-alkyl C1-, C2-, C3-, C4-, C5-, C6-, C7-, C8,- C9- or C10-alkyl; and $C_{1-8}$-alkyl C1-, C2-, C3-, C4-, C5-, C6-, C7-, C8,- C9-, C10-, C11-, C12-, C13-, C14-, C15-, C16-, C17- or $C_{1-8}$-alkyl. Further $C_{3-4}$-cycloalkyl denominates C3- or C4-cycloalkyl; $C_{3-5}$-cycloalkyl C3-, C4- or C5-cycloalkyl; $C_{3-6}$-cycloalkyl C3-, C4-, C5- or C6-cycloalkyl; $C_{3-7}$-cycloalkyl C3-, C4-, C5-, C6- or C7-cycloalkyl; $C_{3-8}$-cycloalkyl C3-, C4-, C5-, C6-, C7- or C8-cycloalkyl; $C_{4-5}$-cycloalkyl C4- or C5-cycloalkyl; $C_{4-6}$-cycloalkyl C4-, C5- or C6-cycloalkyl; $C_{4-7}$-cycloalkyl C4-, C5-, C6- or C7-cycloalkyl; $C_{5-6}$-cycloalkyl C5- or C6-cycloalkyl; and $C_{5-7}$-cycloalkyl C5-, C6-oder C7-cycloalkyl. With regard to cycloalkyl, cycloalkyl also refers to saturated cycloalkyls, in which 1 or 2 carbon atoms are substituted by a heteroatom, S, N or O. Cycloalkyl also refers to once or multi, preferably, unsaturated cycloalkyl without a heteroatom in the ring, as long as the cycloalkyl is not aromatic. Preferably the alkyl- or cycloalkyl-residues are methyl, ethyl, vinyl(ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-di-methylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantlyl, $CHF_2$, $CF_3$ or $CH_2OH$, as well as pyrazolinone, oxopyrazolinone [1,4]dioxane or dioxolane.

In connection with alkyl and cycloalkyl, if not defined otherwise, the term "substituted" within the context of the present invention is understood to mean the replacement of an hydrogen atom by F, Cl, Br, I, $NH_2$, SH or OH, and the phrase "multiply substituted" radicals is understood to mean that the substitution takes place multiply with the same or different substituents on different as well as on the same atoms, for example triple substitution on the same C atom as in the case of $CF_3$ or at different positions as in the case of —CH(OH)—CH=CH—$CHCl_2$. Particularly preferred substituents in this connection are F, Cl and OH.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, etc.

The term aryl radical is understood to mean ring systems with at least one aromatic ring but without heteroatoms in also only one of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring, which contain one or more heteroatoms from the group comprising nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

The term substituted in connection with aryl and heteroaryl is understood to denote the substitution of the aryl or heteroaryl with $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{23}$ denotes H, a $C_{1-10}$-alkyl radical, preferably a $C_{1-6}$-alkyl radical, an aryl or heteroaryl radical or an aryl or heteroaryl radical bonded via a $C_{1-3}$-alkylene group, wherein these aryl and heteroaryl radicals may not themselves be substituted by aryl or heteroaryl radicals. The radicals $R^{24}$ and $R^{25}$, which are identical or different, denote H, a $C_{1-10}$-alkyl radical, preferably a $C_{1-6}$-alkyl radical, an aryl radical, a heteroaryl radical or an aryl or heteroaryl radical bonded via a $C_{1-3}$-alkylene group, wherein these aryl and heteroaryl radicals may not themselves be substituted by aryl or heteroaryl radicals. Alternatively, the radicals $R^{24}$ and $R^{25}$ together denote $CH_2CH_2OCH_2CH_2$, $CH_2CH_2NR^{26}CH_2CH_2$, or $(CH_2)_{3-6}$. The radical $R^{26}$ denotes H, a $C_{1-10}$-alkyl radical, preferably a $C_{1-6}$-alkyl radical, an aryl or heteroaryl radical, or an aryl or heteroaryl radical bonded via a $C_{1-3}$-alkylene group, wherein these aryl and heteroaryl radicals may not themselves be substituted with aryl or heteroaryl radicals.

The term salt means any form of the active constituent according to the invention in which this adopts an ionic form or is charged and is coupled to a counterion (a cation or anion), and is present in solution. The term is also understood to include complexes of the active constituent with other molecules and ions, in particular complexes that are complexed via ionic interactions.

The term physiologically compatible salt with cations or bases is understood within the context of the present invention to mean salts of at least one of the compounds according to the invention—generally of a (deprotonated) acid—as an anion of at least one, preferably inorganic cation, that are physiologically compatible, especially when used in humans and/or mammals. Particularly preferred are the salts of alkali and alkaline earth metals, but also with $NH_4^+$, and in particular (mono) or (di)sodium, (mono) or (di)potassium, magnesium or calcium salts.

The term physiologically compatible salt with anions or acids is understood within the context of the present invention to mean salts of at least one of the compounds according to the invention—generally protonated, for example on the nitrogen atom—as a cation with at least one anion, that are physiologically compatible, especially when used in humans and/or mammals. In the context of the present invention the term is particularly understood to denote the salt formed with a physiologically compatible acid, namely salts of the respective active constituent with inorganic or organic acids, that are physiologically compatible, especially when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol $1\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

In a preferred embodiment of a derivative according to the invention R is selected from phenyl, benzyl or phenyl condensed with a heteroaryl, mono-or multisubstituted or unsubstituted respectively. Preferably, R is selected from phenyl, benzyl or phenyl condensed with a heteroaryl, unsubstituted or mono- or disubstituted with OH, F, Cl, Br, I, —$CF_3$, —$OCH_3$, —$OC_2H_5$, —$CH_3$, —$C_2H_5$; even more preferably, R is selected from p-nitrophenyl, 4-nitrobenzyl, unsubstituted benzyl, unsubstituted phenyl, m-trifluoromethylphenyl, p-trifluoromethylphenyl; or phenyl, unsubstituted or monosubstituted with Cl, condensed with =N—O—N=, =N—O—CH=, =N—S—CH=, =N—S—CBr=, —N=CH—NH— or —N=CH—S—.

In a preferred embodiment of a derivative according to the invention R' is selected from ribose, mono-or multisubstituted or unsubstituted; $C_{1-6}$-alkyl saturated or unsaturated, mono-or multisubstituted or unsubstituted; $C_{3-8}$-cycloalkyl or $C_{3-8}$-cycloalkyl containing 1 or 2 heteroatoms selected from S, O or N in the ring, mono-or multisubstituted or unsubstituted respectively; benzyl, mono-or multisubstituted or unsubstituted; or $C_{4-6}$-alkyl-O—R" with alkyl saturated and unsubstituted and R" selected from $C_{3-8}$-cycloalkyl or $C_{3-8}$-cycloalkyl containing 1 or 2 heteroatoms selected from S, O or N in the ring, mono-or multisubstituted or unsubstituted respectively. More preferably, R' is selected from ribose, mono- or disubstituted or unsubstituted; $C_{3-6}$-alkyl, saturated and unsubstituted or substituted with F, Cl, Br, I or OH; $C_{5-7}$-cycloalkyl or $C_{5-7}$-cycloalkyl containing 1 or 2 heteroatoms selected from S, O or N in the ring, mono-or disubstituted or unsubstituted respectively; benzyl, mono- or disubstituted or unsubstituted; or $C_{4-6}$-alkyl-O—R" with alkyl saturated and unsubstituted and R" selected from $C_{3-8}$-cycloalkyl containing 1 or 2 heteroatoms selected from S, O or N in the ring, mono-or disubstituted or unsubstituted respectively. Even more preferably, R' is selected from ribose, unsubstituted; n-butyl or butan-4-ol; cyclopentyl, tetrahydrofuranyl or tetrahydropyranyl, unsubstituted respectively; benzyl, unsubstituted or mono- or disubstituted with $NO_2$, F, phenyl, I, Cl, trifluoromethoxy, trifluoromethyl or methoxy; or -butyl-O-tetrahydropyranyl.

In a preferred embodiment of a derivative according to the invention Y is selected from H or Cl.

In a preferred embodiment of a derivative according to the invention X is selected from N.

In a preferred embodiment the derivative is selected from the following group:

2-[6-(Benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(Benzo[1,2,5]oxadiazol-5-ylmethylsulfanyl)-purin-9-yl]-5-hydroxymethyl-tetrahydro-furan-3,4-diol 2-[6-(Benzo[1,2,5]oxadiazol-4-ylmethylsulfanyl)-purin-9-yl]-5-hydroxymethyl-tetrahydro-furan-3,4-diol 2-[6-(5-Chloro-benzo[1,2,5]oxadiazol-4-ylmethylsulfanyl)-purin-9-yl]-5-hydroxymethyl-tetrahydro-furan-3,4-diol 2-[6-(Benzo[c]isoxazol-5-ylmethylsulfanyl)-purin-9-yl]-5-hydroxymethyl-tetrahydro-furan-3,4-diol 2-[6-(Benzo[c]isoxazol-7-ylmethylsulfanyl)-purin-9-yl]-5-hydroxymethyl-tetrahydro-furan-3,4-diol 2-[6-(Benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(3H-Benzoimidazol-5-ylmethylsulfanyl)-purin-9-yl]-5-hydroxymethyl-tetrahydro-furan-3,4-diol 2-[6-(3H-Benzoimidazol-4-ylmethylsulfanyl)-purin-9-yl]-5-hydroxymethyl-tetrahydro-furan-3,4-diol 2-[6-(Benzothiazol-6-ylmethylsulfanyl)-purin-9-yl]-5-hydroxymethyl-tetrahydro-furan-3,4-diol 6-(4-Nitro-benzylsulfanyl)-9-(tetrahydro-furan-2-yl)-9H-purine 6-(4-Nitro-benzylsulfanyl)-9-(tetrahydro-pyran-2-yl)-9H-purine 6-(4-Nitro-benzylsulfanyl)-9-[4-(tetrahydro-pyran-2-yloxy)-butyl]-9H-purine 4-[6-(4-Nitro-benzylsulfanyl)-purin-9-yl]-butan-1-ol 9-Cyclopentyl-6-(4-nitro-benzylsulfanyl)-9H-purine 9-Butyl-6-(4-nitro-benzylsulfanyl)-9H-purine 6-(Benzo[1,2,5]oxadiazol-4-ylmethylsulfanyl)-9-butyl-9H-purine 6-(Benzo[c]isothiazol-5-ylmethylsulfanyl)-9-butyl-9H-purine 6-(3-Bromo-benzo[c]isothiazol-5-ylmethylsulfanyl)-9-butyl-9H-purine 2-(7-Benzylsulfanyl-5-chloro-imidazo[4,5-b]pyridin-3-yl)-5-hydroxymethyl-tetrahydro-furan-3,4-diol 2-[5-Chloro-7-(4-nitro-benzylsulfanyl)-imidazo[4,5-b]pyridin-3-yl]-5-hydroxymethyl-tetrahydro-furan-3,4-diol 3-[6-(4-Nitro-benzylsulfanyl)-purin-9-yl]-propan-1-ol 9-Benzyl-6-(4-nitro-benzylsulfanyl)-9H-purine 2-Hydroxymethyl-5-(6-phenethylsulfanyl-purin-9-yl)-tetrahydro-furan-3,4-diol 6-(3-Trifluoromethoxy-benzylsulfanyl)-9H-purine 9-Benzyl-6-(3-trifluoromethoxy-benzylsulfanyl)-9H-purine 6-(4-Trifluoromethoxy-benzylsulfanyl)-9H-purine 9-Benzyl-6-(4-trifluoromethoxy-benzylsulfanyl)-9H-purine 9-(4-Nitro-benzyl)-6-(4-trifluoromethoxy-benzylsulfanyl)-9H-purine 9-(2,3-Difluoro-benzyl)-6-(4-nitro-benzylsulfanyl)-9H-purine 9-(2,4-Difluoro-benzyl)-6-(4-nitro-benzylsulfanyl)-9H-purine 9-(2,5-Difluoro-benzyl)-6-(4-nitro-benzylsulfanyl)-9H-purine 9-(2,6-Difluoro-benzyl)-6-(4-nitro-benzylsulfanyl)-9H-purine 9-Biphenyl-2-ylmethyl-6-(4-nitro-benzylsulfanyl)-9H-purine 9-(4-Iodo-benzyl)-6-(4-nitro-benzylsulfanyl)-9H-purine 9-(3,4-Difluoro-benzyl)-6-(4-nitro-benzylsulfanyl)-9H-purine 9-(3,5-Difluoro-benzyl)-6-(4-nitro-benzylsulfanyl)-9H-purine 9-(3-Fluoro-benzyl)-6-(4-nitro-benzylsulfanyl)-9H-purine 9-(2-Fluoro-benzyl)-6-(4-nitro-benzylsulfanyl)-9H-purine 9-(2,6-Dichloro-benzyl)-6-(4-nitro-benzylsulfanyl)-9H-purine 6-(4-Nitro-benzylsulfanyl)-9-(4-trifluoromethoxy-benzyl)-9H-purine 9-(4-Fluoro-benzyl)-6-(4-nitro-benzylsulfanyl)-9H-purine 9-(2-Chloro-benzyl)-6-(4-nitro-benzylsulfanyl)-9H-purine 6-(4-Nitro-benzylsulfanyl)-9-(3-trifluoromethyl-benzyl)-9H-purine 9-(4-Chloro-benzyl)-6-(4-nitro-benzylsulfanyl)-9H-purine 9-(4-Methoxy-benzyl)-6-(4-nitro-benzylsulfanyl)-9H-purine 9-(3-Methoxy-benzyl)-6-(4-nitro-benzylsulfanyl)-9H-purine and 9-(3,5-Dimethoxy-benzyl)-6-(4-nitro-benzylsulfanyl)-9H-purine.

The derivatives of nitrobenzylthioinosine according to the invention are nontoxic and are surprisingly effective in the treatment of pain and in other indications. Therefore, a further object of the invention is a pharmaceutical composition comprising at least one derivative of nitrobenzylthioinosine according to the invention as active ingredient as well as optionally at least one auxiliary material and/or additive.

The auxiliary material and/or additive can be selected from carriers, excipients, support materials, glidants, fillers, solvents, diluents, colorants, taste conditioners like sugars, antioxidants and/or binders. In the case of a suppository this might involve waxes or fatty acid esters or conserving agents, emulsifiers and/or carriers for parenteral application. The selection of these auxiliary materials and/or additives and of the amounts to be used depends upon how the pharmaceutical composition is to be applied.

Examples include here oral or parenteral like pulmonal, nasal, rectal and/or intravenous application. Therefore the pharmaceutical composition according to the invention can be adapted for topical or systemical application, especially dermal, subcutaneous, intramuscular, intra-articular and/or intraperitoneal, pulmonal, buccal, sublingual, nasal, percutaneous, vaginal, oral or parenteral, pulmonal, nasal, rectal and/or intravenous application.

For treatment the pharmaceutical composition according to the invention might preferrably be in the form of a plaster and/or gauze providing an occlusion of burned or wounded skin.

For oral application preparations in the form of tablets, chewable tablets, dragees, capsules, granules, drops, juices and syrups are suitable. Solutions, suspensions, readily reconstitutable dry preparations and sprays are suitable e.g. for parenteral application. The compounds according to the invention as a deposit in a dissolved form or in a patch, optionally with the addition of agents which promote dermal penetration, are examples of suitable percutaneous forms of application. Dermal applications include e.g. an ointment, a gel, a cream, a lotion, a suspension, an emulsion whereas the preferred form for rectal application is a suppository. Therefore, in a preferred object of the invention the pharmaceutical composition according to the invention is in the form of an ointment, a gel, a cream, a lotion, a suspension, an emulsion, a suppository, a solution, a tablet, a chewable tablet, a dragee, a capsule, a granules, drops, a juice and/or a syrup.

The compounds according to the invention can be released in a delayed manner from forms of preparations which can be applied as mentioned above, especially orally, rectally or percutaneously. Retard formulations are preferred for the invention.

The amount of active ingredient to be administered to the patient varies depending on the weight of the patient, on the type of application, on the indication and on the severity of the illness. 1 to 500 mg of the active ingredient are usually applied per kg of patient weight.

In a preferred embodiment of the invention a pharmaceutical composition containing containing from 0.05 to 90% of active ingredient is provided.

The derivatives of nitrobenzylthioinosine according to the invention are surprisingly effective in the treatment of pain and in other indications. Therefore a further embodiment of the invention comprises the use of a derivatives of nitrobenzylthioinosine according to the invention for the treatment of pain, especially acute, chronic and/or neuropathic pain.

A further embodiment of the invention comprises the use of a derivatives of nitrobenzylthioinosine according to the invention for the treatment of epilepsy and other CNS-related disorders as well as for neuroprotection or cardioprotection.

Furthermore the invention relates to a method of treatment using derivatives of nitrobenzylthioinosine according to the invention especially for the treatment of pain, especially acute, chronic and/or neuropathic pain; the treatment of epilepsy and other CNS-related disorders as well as for neuroprotection or cardioprotection.

The following examples are provided for description purposes only. The examples and the language used herein further illustrate the invention and are not intended to be limiting and should not be understood to be limiting the scope of the claims appended hereto.

EXAMPLES

Example 0

Basic Synthesis

Remark:

All examples 1 to 25 and 27 were synthesized according to Example 53. Examples 26 and 28 to 51 were synthesized according to or in variation of the following synthesis A to C.

Synthesis A:

Synthesis of 9-benzyl-6-(4-nitrobenzylthio)-purine, two steps.

6-(4-Nitrobenzylthio)-purine

After stirring a mixture of 30 mmol of 6-mercaptopurine monohydrate (5.12 g) and 30 mmol of water-free $K_2CO_3$ (4.12 g) in 25 mL of dry DMF for 5 minutes, 30 mmol of 4-nitrobenzylbromide (6.48 g) was added. After stirring for 4 h, 200 mL of $H_2O$ was added. The obtained solid was filtered and washed with EtOAc and $CH_2Cl_2$, followed by drying under vacuum. Yield: 91%.—White powder.

M.p. 239° C. (Dec.), Lit.: 244-247° C.[1]; 262° C.[2].–1H NMR (DMSO-d6) d=4.80 (s, 2H, $CH_2S$), 7.76 (d, J=8.8, 2H, CH Ph), 8.18 (d, J 8.8, 2H, CH Ph), 8.48 (s, 1H, H-2), 8.74 (s, 1H, H-8).-13C NMR (DMSO-d6) d=30.7, 123.5, 129.2, 130.2, 143.7, 146.5, 146.6, 150.5, 151.4, 156.5.

9-Benzyl-6-(4-nitrobenzylthio)-purine 1 mmol of 6-(4-nitrobenzylthio)-purine (0.29 g) was added to a suspension of 1 mmol of NaH (60% dispersion in mineral oil; 40 mg) in 4 mL of dry DMF.

After addition of 1.2 mmol of benzylbromide (205 mg; 143 mL), the reaction was stirred overnight. After addition of 15 mL of $H_2O$, the product was extracted with EtOAc (3×15 mL). The combined organic layers were dried ($MgSO_4$) and the solvent was evaporated. The crude product was purified by column chromatography (silica; pet. ether 40-60/EtOAc 1/1, v/v).

Synthesis B:

Synthesis of 6-(3-Trifluoromethoxybenzylsulfanyl)-purine 6-(3-Trifluoromethoxybenzylsulfanyl)-purine After stirring a mixture of 30 mmol of 6-mercaptopurine monohydrate (5.12 g) and 30 mmol of water-free $K_2CO_3$ (4.12 g) in 25 mL of dry DMF for 5 minutes, 30 mmol of 4-trifluormethoxybenzylbromide (6.48 g) was added. After stirring for 4 h, 200 mL of $H_2O$ was added. The obtained solid was filtered and washed with EtOAc and $CH_2Cl_2$, followed by drying under vacuum.

Synthesis C:

Synthesis of 6-Benzyl-(3-Trifluoromethoxybenzylsulfanyl)-purine, two steps 6-(3-Trifluoromethoxybenzylsulfanyl)-purine After stirring a mixture of 30 mmol of 6-mercaptopurine monohydrate (5.12 g) and 30 mmol of water-free $K_2CO_3$ (4.12 g) in 25 mL of dry DMF for 5 minutes, 30 mmol of 4-trifluormethoxybenzylbromide (6.48 g) was added. After stirring for 4 h, 200 mL of $H_2O$ was added. The obtained solid was filtered and washed with EtOAc and $CH_2Cl_2$, followed by drying under vacuum.

9-Benzyl-6-(3-Trifluoromethoxybenzylsulfanyl)-purine 1 mmol of 6-(3-Trifluoromethoxybenzylsulfanyl)-purine (0.29 g) was added to a suspension of 1 mmol of NaH (60% dispersion in mineral oil; 40 mg) in 4 mL of dry DMF.

After addition of 1.2 mmol of benzylbromide (205 mg; 143 mL), the reaction was stirred overnight. After addition of 15 mL of $H_2O$, the product was extracted with EtOAc (3×15 mL). The combined organic layers were dried ($MgSO_4$) and the solvent was evaporated. The crude product was purified by column chromatography (silica; pet. ether 40-60/EtOAc 1/1, v/v).

Example 1

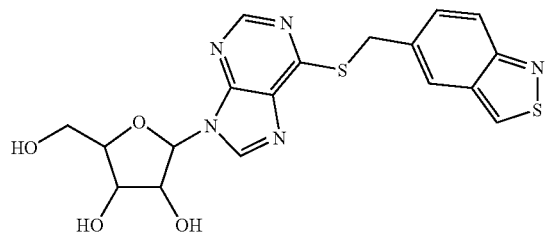

2-[6-(Benzo[c]isothiazol-5-ylmethylsulfanyl)-purin-9-yl]-5-hydroxymethyl-tetrahydro-furan-3,4-diol Synthesized according to Example 53.

Example 2

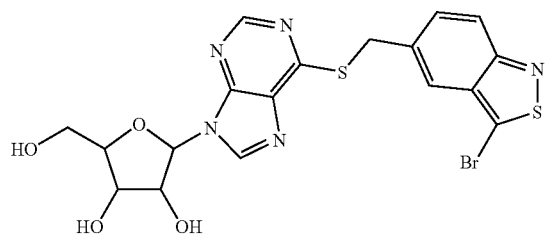

2-[6-(3-Bromo-benzo[c]isothiazol-5-ylmethylsulfanyl)-purin-9-yl]-5-hydroxymethyl-tetrahydro-furan-3,4-diol Synthesized according to Example 53.

Example 3

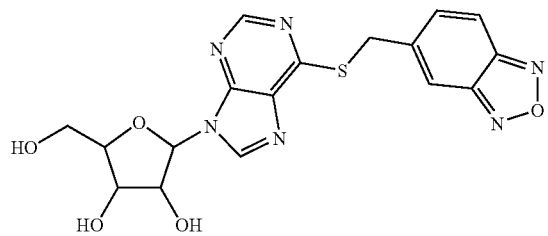

2-[6-(Benzo[1,2,5]oxadiazol-5-ylmethylsulfanyl)-purin-9-yl]-5-hydroxymethyl-tetrahydro-furan-3,4-diol Synthesized according to Example 53.

Example 4

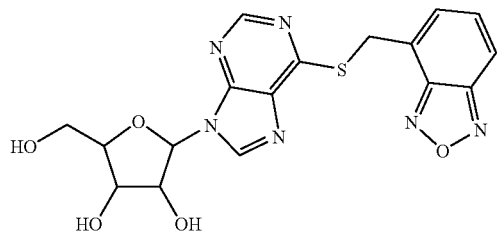

2-[6-(Benzo[1,2,5]oxadiazol-4-ylmethylsulfanyl
purin-9-yl]-5-hydroxymethyl-tetrahydro-furan-3,4-
diol Synthesized according to Example 53.

Example 5

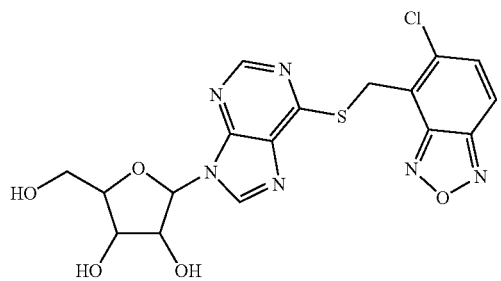

2-[6-(5-Chloro-benzo[1,2,5]oxadiazol-4-ylmethyl-
sulfanyl)-purin-9-yl]-5-hydroxymethyl-tetrahydro-
furan-3,4-diol Synthesized according to Example 53.

Example 6

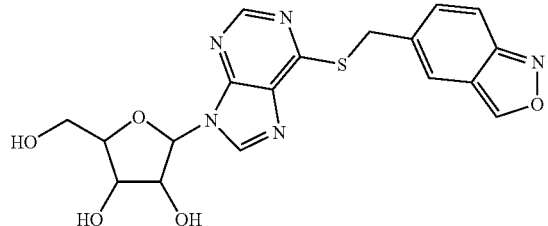

2-[6-(Benzo[c]isoxazol-5-ylmethylsulfanyl)-purin-9-
yl]-5-hydroxymethyl-tetrahydro-furan-3,4-diol Synthesized according to Example 53.

Example 7

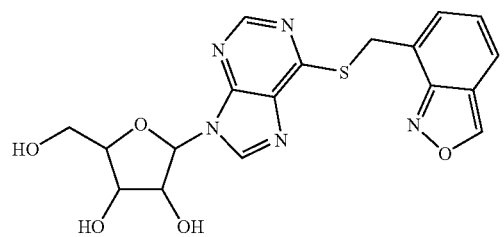

2-[6-(Benzo[c]isoxazol-7-ylmethylsulfanyl)-purin-9-
yl]-5-hydroxy methyl-tetrahydro-furan-3,4-diol Synthesized according to Example 53.

Example 8

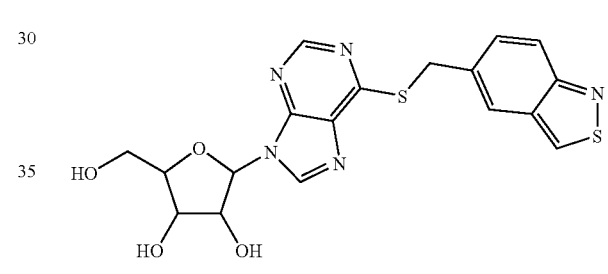

2-[6-(Benzo[c]isothiazol-5-ylmethylsulfanyl)-purin-
9-yl]-5-hydroxy methyl-tetrahydro-furan-3,4-diol Synthesized according to Example 53.

Example 9

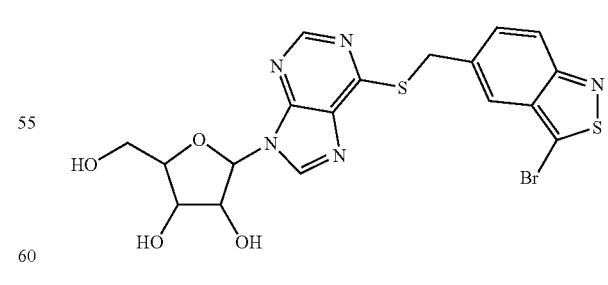

2-[6-(3-Bromo-benzo[c]isothiazol-5-ylmethylsulfa-
nyl)-purin-9-yl]-5-hydroxymethyl-tetra hydro-furan-
3,4-diol Synthesized according to Example 53.

Example 10

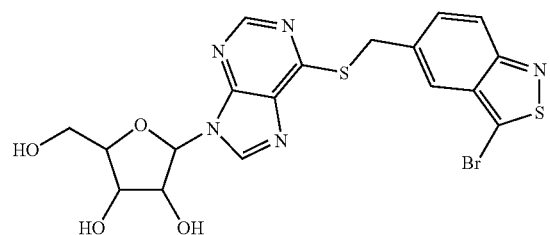

2-[6-(3-Bromo-benzo[c]isothiazol-5-ylmethylsulfanyl)-purin-9-yl]-5-hydroxymethyl-tetra hydro-furan-3,4-diol Synthesized according to Example 53.

Example 11

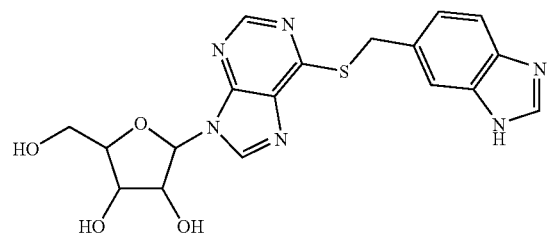

2-[6-(3H-Benzoimidazol-5-ylmethylsulfanyl)-purin-9-yl]-5-hydroxymethyl-tetra hydro-furan-3,4-diol Synthesized according to Example 53.

Example 12

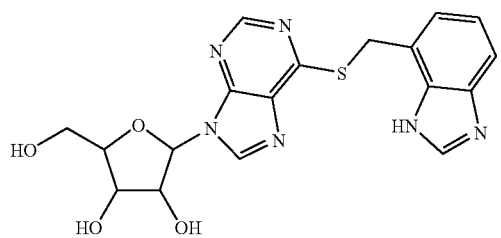

2-[6-(3H-Benzoimidazol-4-ylmethylsulfanyl)-purin-9-yl]-5-hydroxymethyl-tetrahydro-furan-3,4-diol Synthesized according to Example 53.

Example 13

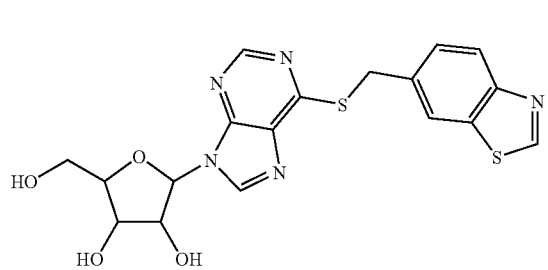

2-[6-(Benzothiazol-6-ylmethylsulfanyl)-purin-9-yl]-5-hydroxymethyl-tetrahydro-furan-3,4-diol Synthesized according to Example 53.

Example 14

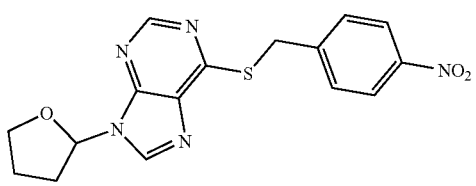

6-(4-Nitro-benzylsulfanyl)-9-(tetrahydro-furan-2-yl)-9H-purine

Synthesized according to Example 53.

Example 15

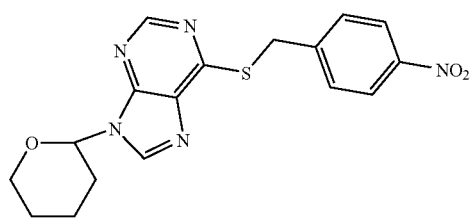

6-(4-Nitro-benzylsulfanyl)-9-(tetrahydro-pyran-2-yl)-9H-purine

Synthesized according to Example 53.

Example 16

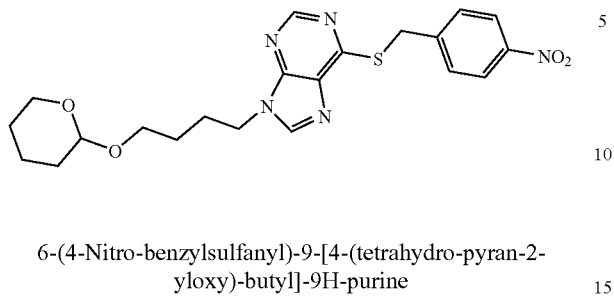

6-(4-Nitro-benzylsulfanyl)-9-[4-(tetrahydro-pyran-2-yloxy)-butyl]-9H-purine

Synthesized according to Example 53.

Example 17

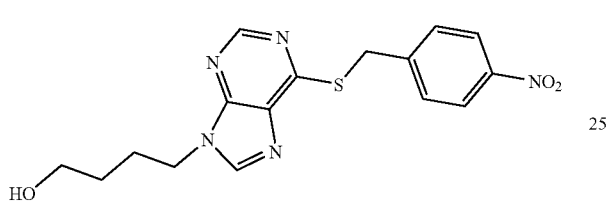

4-[6-(4-Nitro-benzylsulfanyl)-purin-9-yl]-butan-1-ol

Synthesized according to Example 53.

Example 18

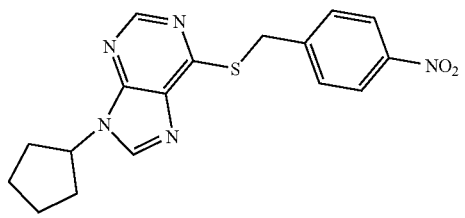

9-Cyclopentyl-6-(4-nitro-benzylsulfanyl)-9H-purine

Synthesized according to Example 53.

Example 19

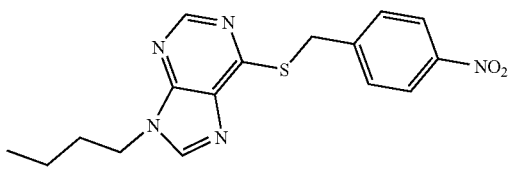

9-Butyl-6-(4-nitro-benzylsulfanyl)-9H-purine

Synthesized according to Example 53.

Example 20

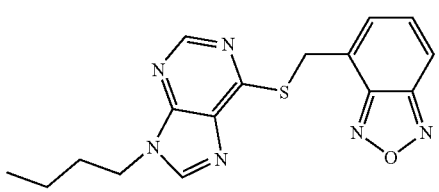

6-(Benzo[1,2,5]oxadiazol-4-ylmethylsulfanyl)-9-butyl-9H-purine

Synthesized according to Example 53.

Example 21

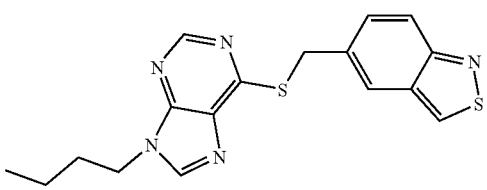

6-(Benzo[c]isothiazol-5-ylmethylsulfanyl)-9-butyl-9H-purine

Synthesized according to Example 53.

Example 22

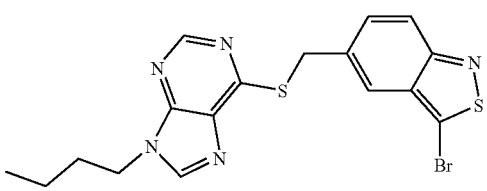

6-(3-Bromo-benzo[c]isothiazol-5-ylmethylsulfanyl)-9-butyl-9H-purine

Synthesized according to Example 53.

Example 23

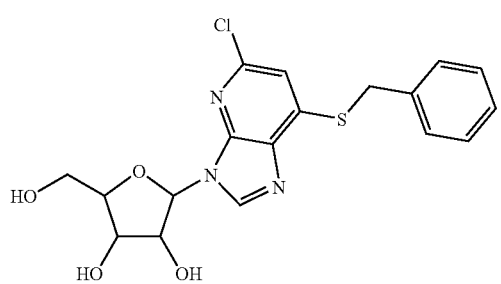

2-(7-Benzylsulfanyl-5-chloro-imidazo[4,5-b]pyridin-3-yl)-5-hydroxymethyl-tetrahydro-furan-3,4-diol Synthesized according to Example 53.

Example 24

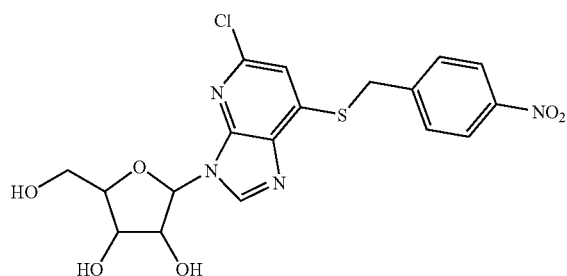

2-[5-Chloro-7-(4-nitro-benzylsulfanyl)-imidazo[4,5-b]pyridin-3-yl]-5-hydroxymethyl-tetrahydro-furan-3,4-diol Synthesized according to Example 53.

Example 25

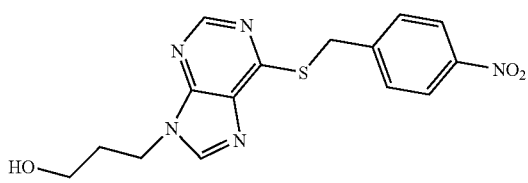

3-[6-(4-Nitro-benzylsulfanyl)-purin-9-yl]-propan-1-ol

Synthesized according to Example 53.

Example 26

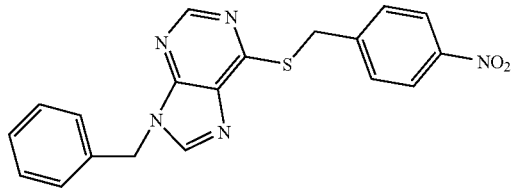

9-Benzyl-6-(4-nitro-benzylsulfanyl)-9H-purine

Synthesized according to Example 0 synthesis A.

Yield: 37%. Yellowish solid. M.p. 139° C.—$^1$H NMR (CDCl$_3$) d=4.73 (s, 2H, CH$_2$S), 5.41 (s, 2H, CH$_2$N), 7.26-7.39 (m, 5H, CH Ph), 7.66 (d, J=8.8, 2H, CH Ph), 7.95 (s, 1H, H-2), 8.15 (d, J=8.8, 2H, CH Ph), 8.77 (s, 1H, H-8).-13C NMR (CDCl$_3$) d=31.6, 47.3, 123.5, 127.7, 128.6, 129.0, 129.9, 130.9, 134.9, 142.8, 145.7, 146.9, 148.7, 151.8, 159.0.-HRMS (ESI) m/z Found: 378.0981

Example 27

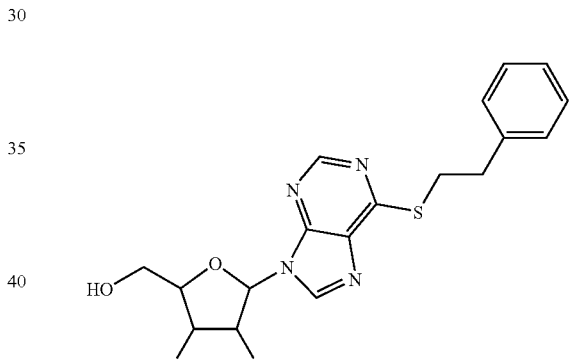

2-Hydroxymethyl-5-(6-phenethylsulfanyl-purin-9-yl)-tetrahydro-furan-3,4-diol

Synthesized according to Example 53.

Example 28

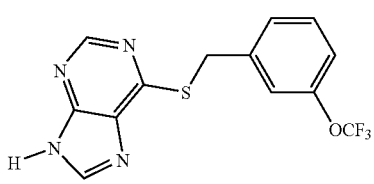

6-(3-Trifluoromethoxy-benzylsulfanyl)-9H-purine

Synthesized according to Example 0 synthesis B.

Example 29

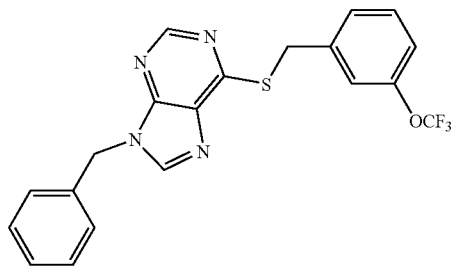

9-Benzyl-6-(3-trifluoromethoxy-benzylsulfanyl)-9H-purine

Synthesized according to Example 0 synthesis C.

Example 30

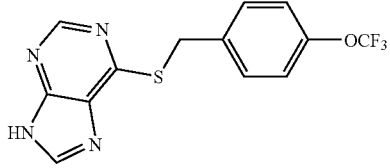

6-(4-Trifluoromethoxy-benzylsulfanyl)-9H-purine

Synthesized according to Example 0 synthesis B; modified by adding 3-trifluormethoxybenzylbromide instead of 4-trifluormethoxybenzylbromide.

Example 31

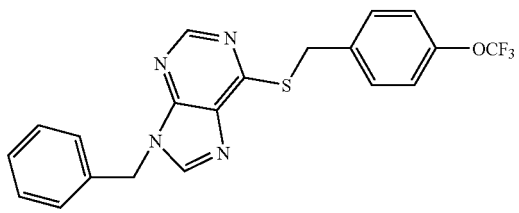

9-Benzyl-6-(4-trifluoromethoxy-benzylsulfanyl)-9H-purine

Synthesized according to Example 0 synthesis C; modified by adding 3-trifluormethoxybenzylbromide instead of 4-trifluormethoxybenzylbromide.

Example 32

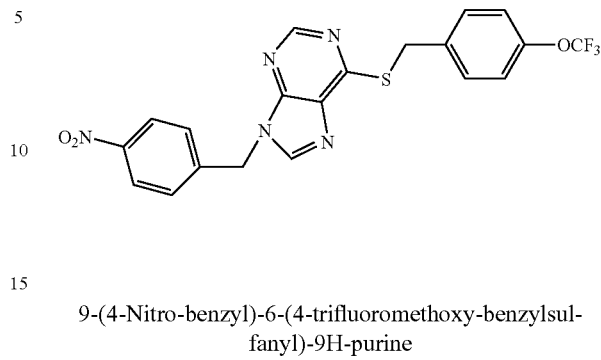

9-(4-Nitro-benzyl)-6-(4-trifluoromethoxy-benzylsulfanyl)-9H-purine

Synthesized according to Example 31; modified by adding 4-nitro-benzylbromide instead of benzylbromide.

Example 33

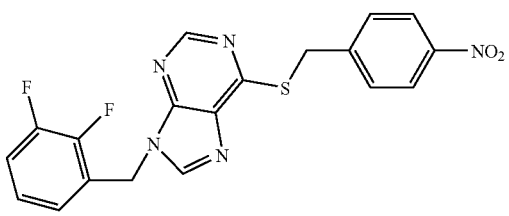

9-(2,3-Difluoro-benzyl)-6-(4-nitro-benzylsulfanyl)-9H-purine

Synthesized according to Example 0; Synthesis A; modified by adding 2,3.difluoro-benzylbromide instead of benzylbromide.

Example 34

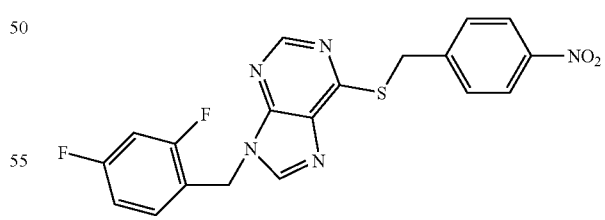

9-(2,4-Difluoro-benzyl)-6-(4-nitro-benzylsulfanyl)-9H-purine

Synthesized according to Example 0; Synthesis A; modified by adding 2,4-difluoro-benzylbromide instead of benzylbromide.

Example 35

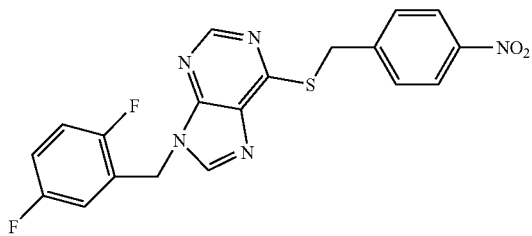

9-(2,5-Difluoro-benzyl)-6-(4-nitro-benzylsulfanyl)-9H-purine

Synthesized according to Example 0; Synthesis A; modified by adding 2,5-difluoro-benzylbromide instead of benzylbromide.

Example 36

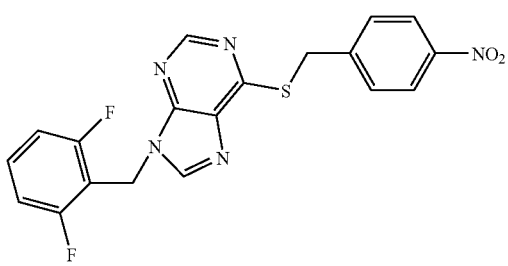

9-(2,6-Difluoro-benzyl)-6-(4-nitro-benzylsulfanyl)-9H-purine

Synthesized according to Example 0; Synthesis A; modified by adding 2,6.difluoro-benzylbromide instead of benzylbromide.

Example 37

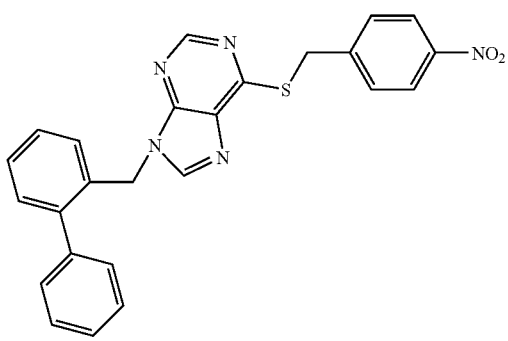

9-Biphenyl-2-ylmethyl-6-(4-nitro-benzylsulfanyl)-9H-purine

Synthesized according to Example 0; Synthesis A; modified by adding 2-phenyl-benzylbromide instead of benzylbromide.

Example 38

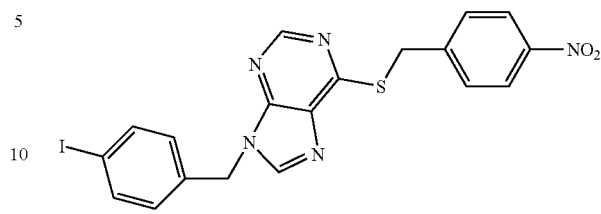

9-(4-Iodo-benzyl)-6-(4-nitro-benzylsulfanyl)-9H-purine

Synthesized according to Example 0; Synthesis A; modified by adding 4-iodo-benzylbromide instead of benzylbromide.

Example 39

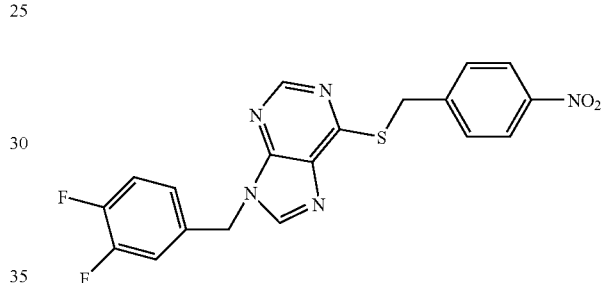

9-(3,4-Difluoro-benzyl)-6-(4-nitro-benzylsulfanyl)-9H-purine

Synthesized according to Example 0; Synthesis A; modified by adding 3,4-difluoro-benzylbromide instead of benzylbromide.

Example 40)

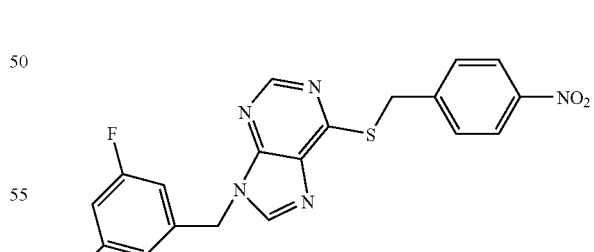

9-(3,5-Difluoro-benzyl)-6-(4-nitro-benzylsulfanyl)-9H-purine

Synthesized according to Example 0; Synthesis A; modified by adding 3,5-difluoro-benzylbromide instead of benzylbromide.

Example 41

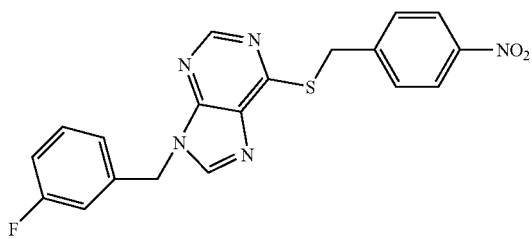

9-(3-Fluoro-benzyl)-6-(4-nitro-benzylsulfanyl)-9H-purine

Synthesized according to Example 0; Synthesis A; modified by adding 3-fluoro-benzylbromide instead of benzylbromide.

Example 42

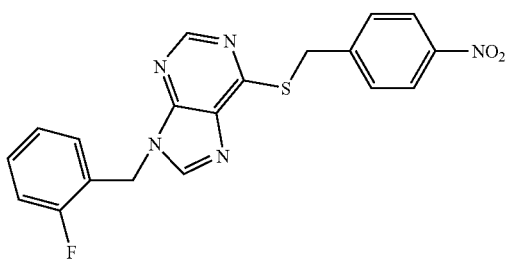

9-(2-Fluoro-benzyl)-6-(4-nitro-benzylsulfanyl)-9H-purine

Synthesized according to Example 0; Synthesis A; modified by adding 2-fluoro-benzylbromide instead of benzylbromide.

Example 43

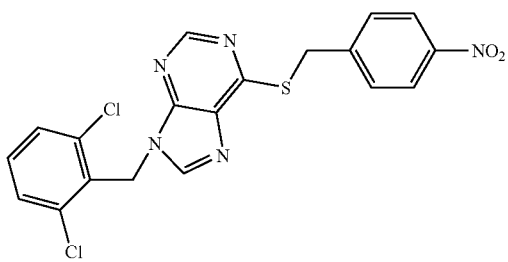

9-(2,6-Dichloro-benzyl)-6-(4-nitro-benzylsulfanyl)-9H-purine

Synthesized according to Example 0; Synthesis A; modified by adding 2,6-dichloro-benzylbromide instead of benzylbromide.

Example 44

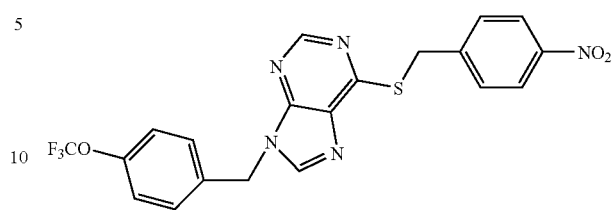

6-(4-Nitro-benzylsulfanyl)-9-(4-trifluoromethoxy-benzyl)-9H-purine

Synthesized according to Example 0; Synthesis A; modified by adding 4-trifluoromethoxy-benzylbromide instead of benzylbromide.

Example 45

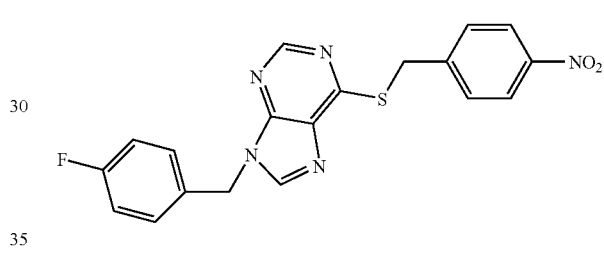

9-(4-Fluoro-benzyl)-6-(4-nitro-benzylsulfanyl)-9H-purine

Synthesized according to Example 0; Synthesis A; modified by adding 4-fluoro-benzylbromide instead of benzylbromide.

Example 46

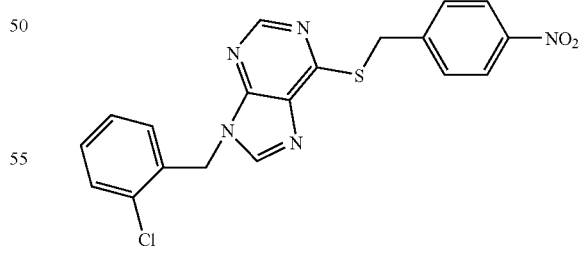

9-(2-Chloro-benzyl)-6-(4-nitro-benzylsulfanyl)-9H-purine

Synthesized according to Example 0; Synthesis A; modified by adding 2-chloro-benzylbromide instead of benzylbromide.

Example 47

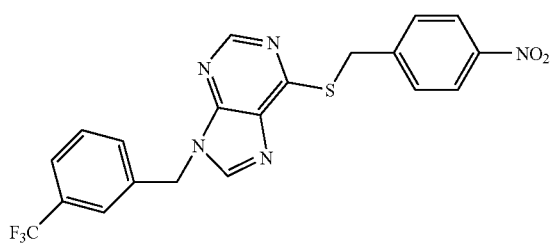

6-(4-Nitro-benzylsulfanyl)-9-(3-trifluoromethyl-benzyl)-9H-purine

Synthesized according to Example 0; Synthesis A; modified by adding 3-trifluormethyl-benzylbromide instead of benzylbromide.

Example 48

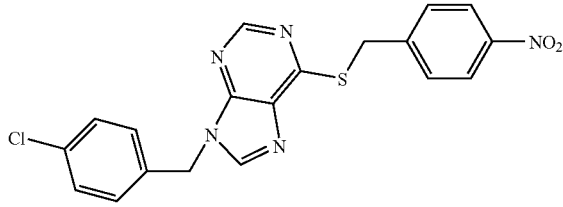

9-(4-Chloro-benzyl)-6-(4-nitro-benzylsulfanyl)-9H-purine

Synthesized according to Example 0; Synthesis A; modified by adding 4-chloro-benzylbromide instead of benzylbromide.

Example 49

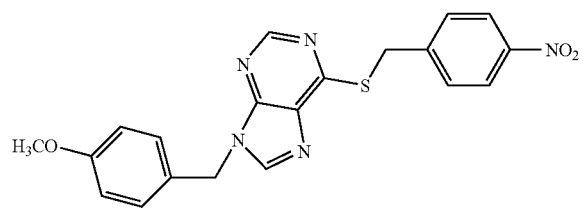

9-(4-Methoxy-benzyl)-6-(4-nitro-benzylsulfanyl)-9H-purine

Synthesized according to Example 0; Synthesis A; modified by adding 4-methoxy-benzylbromide instead of benzylbromide.

Example 50

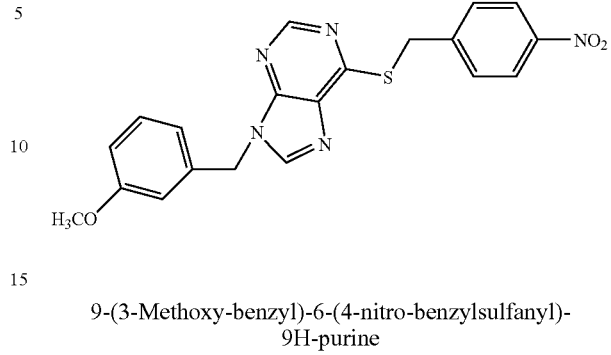

9-(3-Methoxy-benzyl)-6-(4-nitro-benzylsulfanyl)-9H-purine

Synthesized according to Example 0; Synthesis A; modified by adding 3-methoxy-benzylbromide instead of benzylbromide.

Example 51

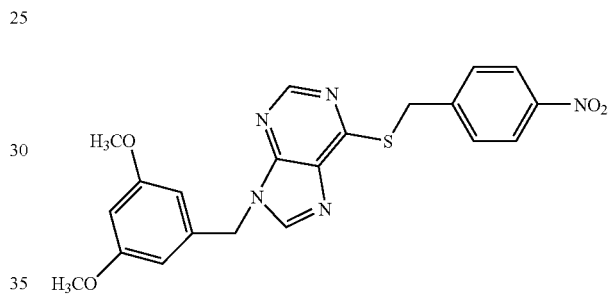

9-(3,5-Dimethoxy-benzyl)-6-(4-nitro-benzylsulfanyl)-9H-purine

Synthesized according to Example 0; Synthesis A; modified by adding 3,5-dimethoxy-benzylbromide instead of benzylbromide.

Example 52

Assay and Data

Assay

All final products according to examples 1-51 were tested in the following radioligandbinding assay: Human erythrocyte membranes were used as a rich source of the nucleoside transport protein with [$^{3H}$]NBTI as the radioligand ($K_D$ value: 0.59±0.07 nM).

100 ml compound or buffer
100 ml [$^3$H]NBTI 1.5 nM
100 ml buffer
    (50 mM Tris.HCl,pH 7.4)
100 ml erythrocyte membranes
After 30 minutes of incubation at 25° C.:
filtration over Whatman GF/C filters
    (50 mM Tris.HCl used for washing)
filters in vials
3.5 ml scintillation fluid
counting in beta counter after 2 hr Data:

| Example | Binding (Nucleoside Transporter (Ki)) |
|---------|----------------------------------------|
| 1  | 108 nM |
| 2  | 42 nM |
| 3  | 10 nM |
| 4  | 1.5 nM |
| 5  | 9.7 nM |
| 6  | 25 nM |
| 7  | 96 nM |
| 8  | 666 nM |
| 9  | 108 nM |
| 10 | 42 nM |
| 11 | 191 nM |
| 12 | 42% (10 μM) |
| 13 | 165 nM |
| 14 | 937 nM |
| 15 | 1200 nM |
| 16 | 488 nM |
| 17 | 1140 nM |
| 18 | 736 nM |
| 19 | 238 nM |
| 20 | 5600 nM |
| 21 | 3100 nM |
| 22 | 682 nM |
| 23 | 670 nM |
| 24 | 47 nM |
| 25 | 130 nM |
| 26 | 135 nM |
| 27 | 12 nM |

Example 53

Further Examples

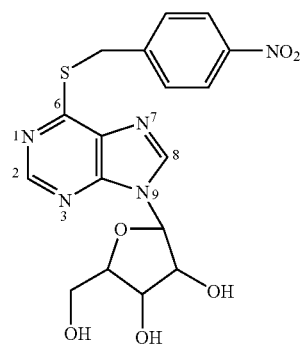

NBTI, 1

Chemical synthesis—The first modification was conversion of the nitro group in the 4-nitrobenzyl moiety to a benzoxadiazole ring system (compounds 14-16, Scheme 1). This is a cyclic functionality, which resembles the nitro group. Cyclocondensation of the appropriate azide (compounds 24) in boiling toluene gave benzofuroxanes (compounds 5-7). (Johnston, T. P.; Holum, L. B.; Montgomery, J. A. J. Amer. Chem. Soc. 1985, 80, 6265-6272).

Refluxing in ethanol in the presence of triethyphosphite resulted in deoxygenation to benzofurazan 8. Benzylic bromination of this compound was done in the presence of N-bromosuccinimide and benzoyl peroxide. (Ghosh, P. B.; Ternai, B.; Whitehouse; M. W. J. Med. Chem. 1972, 15, 255-260 and Ghosh, P. B.; Whitehouse, M. W. J. Med. Chem. 1968, 11, 305-311). Finally coupling of the resulting bromide with 6-mercaptopurine riboside was achieved in DMF at room temperature. (Temple, C.; Kussner, C. L.; Montgomery, J. A. J. Org. Chem. 1968, 11, 41-43).

Scheme 1. Preparation of Bezofurazan Analogs.

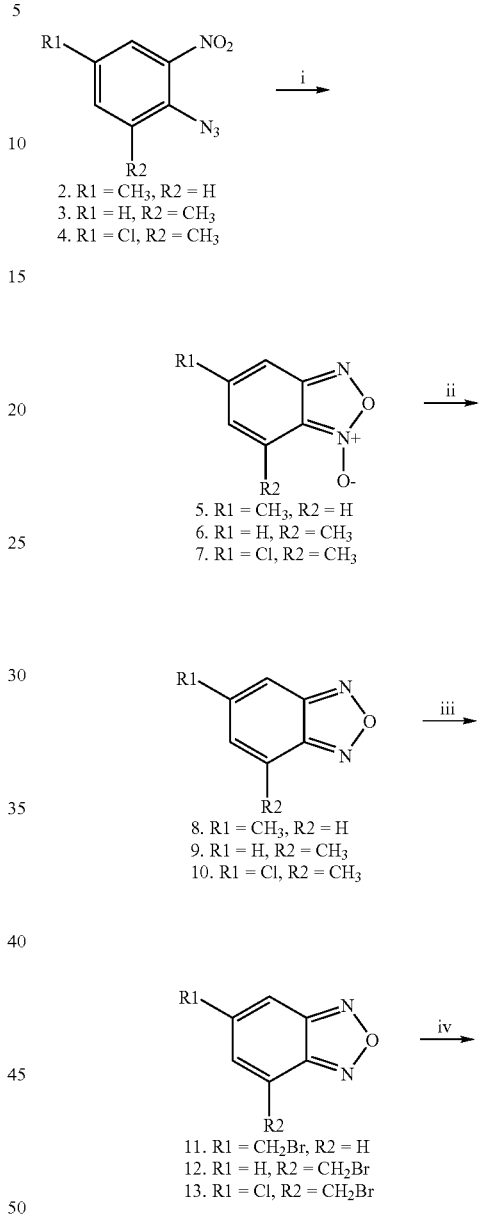

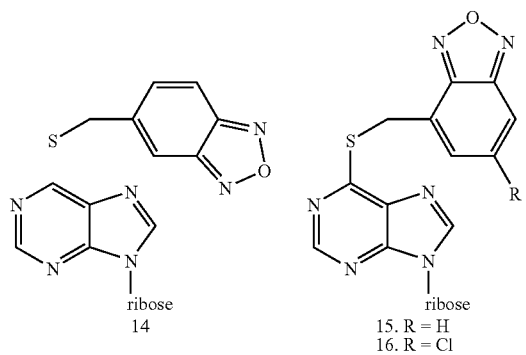

14

15. R = H
16. R = Cl i) Toluene, reflux, 2 h; ii) P(OEt)₃, ethanol, reflux, 30 min; iii) NBS, Bz₂O₂, CCl₄, N₂, reflux, 18 h; iv) 6-mercaptopurine riboside, K₂CO₃, DMF, room temperature.

The next series of analogs of NBTI were compounds 23 and 24 (Scheme 2). These deaza analogs of the benzoxadiazole substituents were obtained by coupling bromomethyl-2,1-benzisoxazole with 6-mercaptopurine riboside. This bromide was prepared by ring closure of the proper ortho-nitrobenzaldehyde (17-18) in the presence of tin(II) chloride and subsequent bromination with NBS. (Phillips, B. T.; Hartman, G. D. J. Heterocyclic Chem. 1986, 23, 897-899).

Scheme 2. Preparation of Benzisoxazole Analogs.

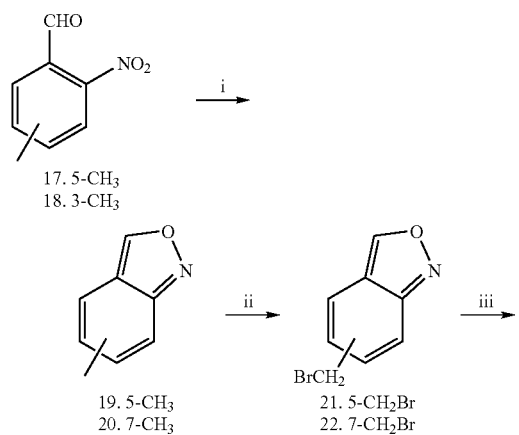

17. 5-CH₃
18. 3-CH₃

19. 5-CH₃
20. 7-CH₃

21. 5-CH₂Br
22. 7-CH₂Br

-continued

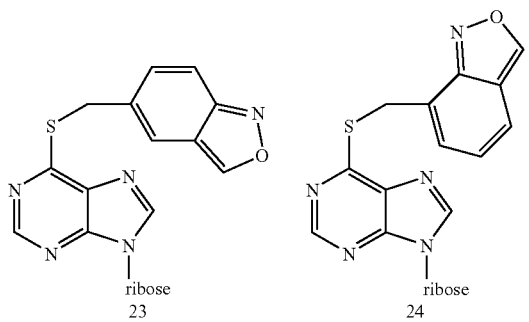

23  24 i) SnCl₂·2H₂O, HCl, 15° C., 2 h; ii) NBS, Bz₂O₂, CCl₄, N₂, reflux, 12 h; iii) 6-mercaptopurine riboside, K₂CO₃, DMF, 2 h.

2,1-Benzoisothiazole analogs were prepared by a general procedure, which involves cyclization of o-toluidines by N-sulfinylmethane sulfonamide (Scheme 3). (Singerman, G. M. J. Heterocyclic Chem 1975, 12, 877-882). Again standard benzylic bromination with NBS afforded the 5-bromomethyl-benz-2,1-isothiazole (27). Subsequent treatment of 26 with n-BuLi and bromine gave bromide 29. Di-bromide 30 was obtained after benzylic bromination of 29.

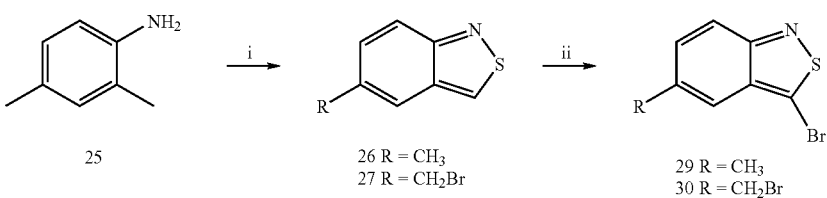

25

26 R = CH₃
27 R = CH₂Br

29 R = CH₃
30 R = CH₂Br

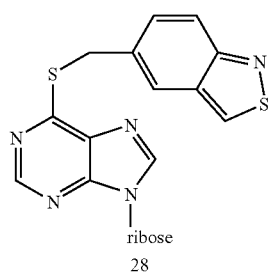

28

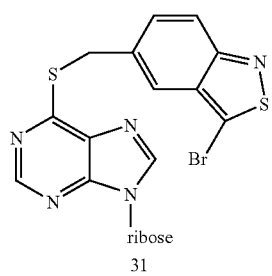

31

Scheme 3. Preparation of Benzoisothiazole Analogs.

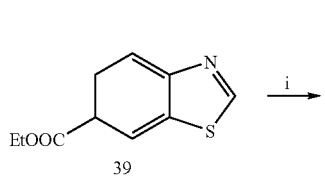

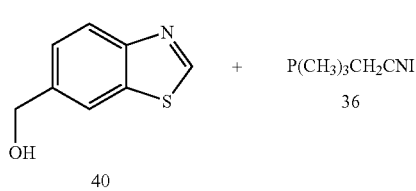

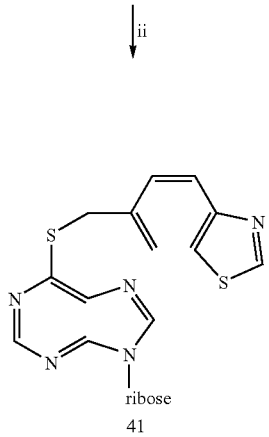

Scheme 4. Preparation of Benzimidazole Analogs.

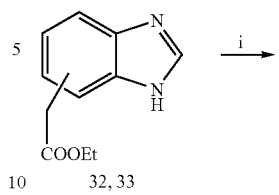

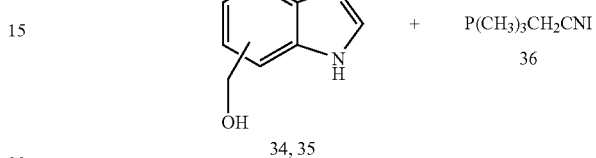

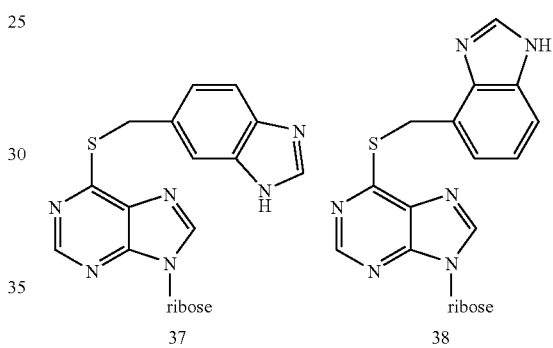

i) CH$_3$SO$_2$NSO, benzene (dry), 0° C. to reflux 18 h; ii) n-BuLi, THF (dry), −78° C., Br$_2$, −78° C. to room temperature; iii) NBS, Bz$_2$O$_2$, CCl$_4$, N$_2$, reflux, 12 h; iv) 6-mercaptopurine riboside, K$_2$CO$_3$, DMF, 2 h.

Benzimidazole analogs were synthesized by a Mitsunobu coupling (Zaragoza, F. Tetrahedron 2001, 57, 5451-5454 and Zaragoza, F.; Stephensen, H. J. Org. Chem. 2001, 66, 2518-2521) of 6-mercaptopurine riboside with benzimidazole-methyl alcohol (Kimura, T.; Takase, Y.; Hayashi, K.; Tanaka, H.; Ohtsuka, I.; Saeki, T.; Kogushi, M.; Yamada, T.; Fujimori, T.; Saitou, I.; Akasaka, K. J. Med. Chem. 1993, 36, 1630-1640), in the presence of (cyanomethyl)trimethylphosphonium iodide (36) and diisopropylethylamine (DIPEA) in propionitrile (Scheme 4). After refluxing of this mixture for 18 hr, water was added and the product precipitated. The direct use of alcohol 34 and 35 is an advantage of this method compared to the previous reactions. (Temple, C.; Kussner, C. L.; Montgomery, J. A. J. Org. Chem. 1968, 11, 41-43). These alcohols were prepared from reduction of the appropriate esters via standard procedures. (Sun, Q.; Gatto, B.; Yu, C.; Liu, A.; Liu, L. F.; LaVoie, E. J. J. Med. Chem. 1995, 38, 3638-3644).

i) LiAlH4/THF, overnight, reflux; ii) 6-mercaptopurine riboside, DIPEA, propionitrile, reflux, 18 h.

The benzothiazole derivative was prepared as shown in Scheme 5. Ethyl benzothiazole-6-carboxylate 39 was prepared by ring closure of ethyl-4-amino-3-mercaptobenzoate. (Burger, A.; Sawhney, S. N. J. Med. Chem. 1968, 11, 270-273). Reduction of this ester under standard conditions at 0° C. gave alcohol 40. (Yadagiri, B.; Lown, J. W. Synth. Commun. 1990, 20, 955-963). Again Mitsunobu coupling of 6-mercaptopurine riboside with 40 gave nucleoside 41 in 56% yield.

Scheme 5. Preparation of Benzothiazole Analogs.

i) LiAlH4/THF, overnight; ii) 6-mercaptopurine riboside, DIPEA, propionitrile, reflux, 18 h.

For the alkylation of the N9 position three methods were used. Reaction of 6-substituted mercaptopurine 42 with 2,3-dihydrofuran or 2,3-dihydro-4H-pyran in the presence of a catalytic amount of p-toluenesulfonic acid led to 43 and 44, respectively (Scheme 6). Such compounds have been described as purine deoxynucleosides. (Robins, R. K.; Godefroi, E. F.; Taylor, E. C.; Lewis, R. L; Jackson, A. J. Am. Chem. Soc. 1960, 83, 2574-79).

Scheme 6. Synthesis of THF- and THP-Protected Compounds.

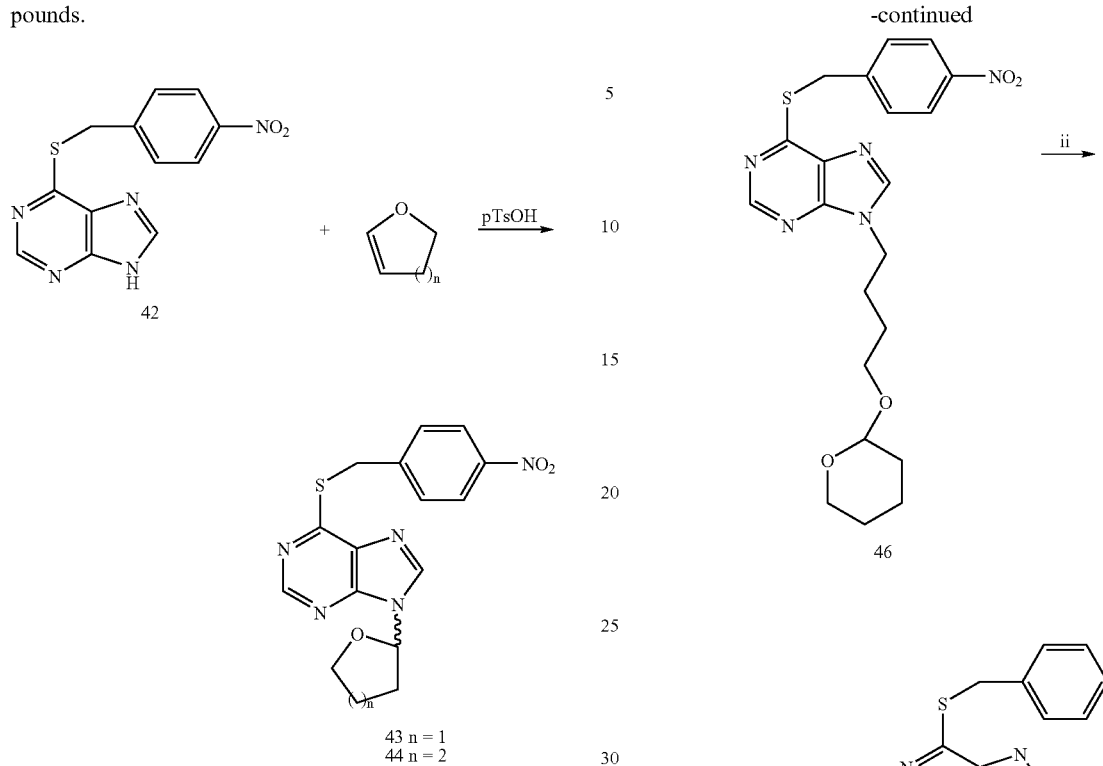

Direct introduction of an alkyl moiety to purine bases at the N9 position was achieved by a Mitsunobu reaction of the proper alcohol and 6-substituted purine 42. (Toyota, A.; Katagiri, N.; Kaneko, C. Synth. Commun. 1993, 23, 1295-1305). One example of such alkylation is illustrated in Scheme 7. Diethyl azodicarboxylate was added in portions to a mixture of purine, alcohol 45 (De Vries, E. F. J.; Steenwinkel, P.; Brussee, J.; Kruse, C. G.; Van der Gen, J. Org. Chem. 1993, 58, 4315-4325), and triphenylphosphine in THF. Since the substituent on C6 is large the main product is the N9 substituted purine 46. Deprotection of the resulting compound with standard procedures gave compound 47. The same method was used for preparation of the N9-cyclopentyl substituted 48.

Scheme 7. Synthesis of Alkyl-Substituted Bases Via a Mitsunobu Reaction.

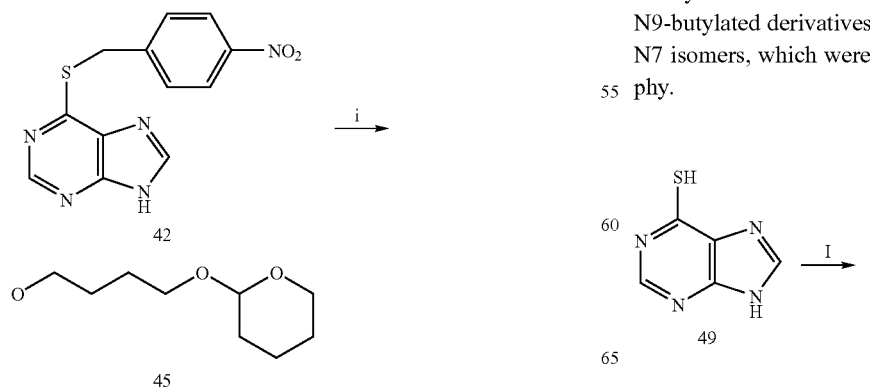

i) DEAD, PPh$_3$, THF (dry); ii) pTSOH, room temperature, 2 h.

For substitution of N9 with an n-butyl group, a solution of the appropriate nucleobase in dry DMF was added dropwise to a suspension of sodium hydride in DMF (Scheme 8). After 30 min, to ensure the complete formation of the anion, n-butyl bromide was added in excess to give the desired N9-butylated derivatives (53-56) with small amounts of the N7 isomers, which were removed by column chromatography.

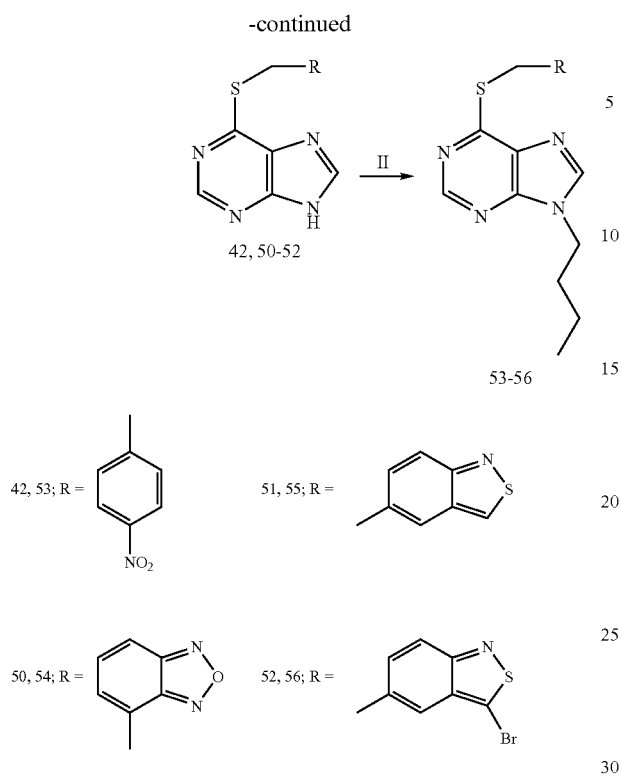

42, 53; R = 4-nitrophenyl 51, 55; R = 5-methylbenzo[c]isothiazole 50, 54; R = 4-methylbenzofurazan 52, 56; R = 5-methyl-3-bromobenzo[c]isothiazole Modification of N1 in the purine ring system was achieved by preparing the 1-deaza-2-chloropurine analog of NBTI. The synthesis of 1-deaza-2-chloropurine has been previously reported. (Cristalli, G.; Grifantini, M.; Vittori, S. Nucleosides & Nucleotides 1985, 4, 621-639). Acetate-protected 2,6-dichloro-1-deazapurine riboside 57 was coupled with benzyl mercaptan in the presence of triethylamine. Deprotection of the sugar with a saturated solution of ammonia in methanol gave the proper nucleoside (Scheme 9).

Scheme 8. Synthesis of N9-Butylated Compounds.

i) Benzyl bromide, K$_2$CO$_3$, DMF, room temperature; ii) NaH, BuBr, DMF, 18 h, room temperature.

Scheme 9. Synthesis of 2-chloro-1-deaza Analogs of NBTI.

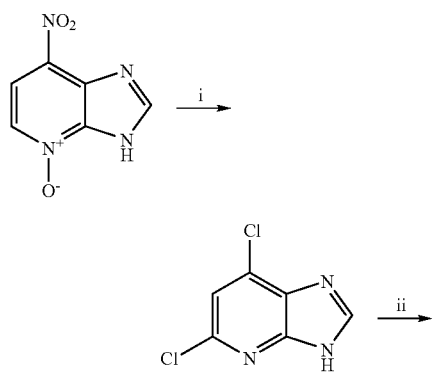

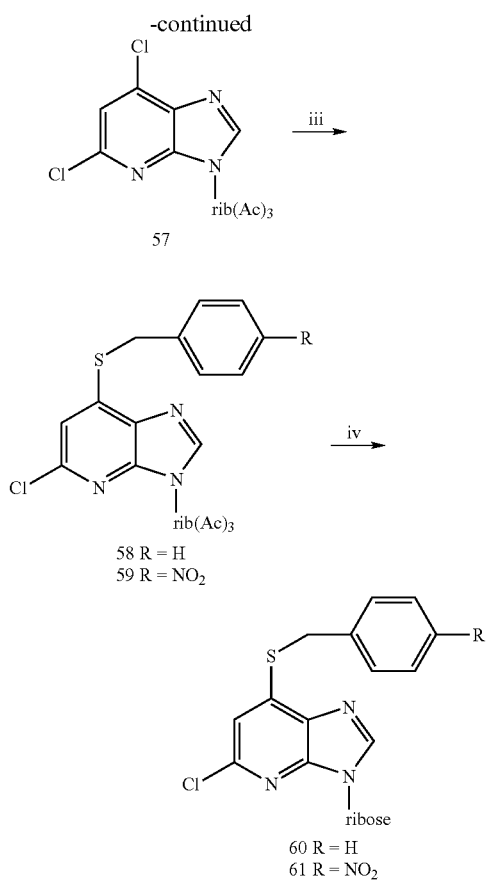

i) POCl$_3$, DMF; ii) 5 nCl$_4$, 1,2,3,5-tetra-O-acetyl-β-D-ribofuranose; iii) 4-nitrobenzylmercaptane, Et$_3$N, DMF, room temperature, 18 hr; iv) NH$_3$/CH$_3$OH, 0° C.

Biological Studies.

All final products were tested in a radioligand binding assay. (I Jzerman, A. P.; Voorschuur, A. H. Naunyn-Schmiedeberg's Arch Pharmacol 1990, 342, 336-341 (and refs therein); Jarvis, S. M. Mol. Pharmacol. 1986, 30, 659-665). Human erythrocyte membranes were used as a rich source of the nucleoside transport protein, with [$^3$H] NBTI as the radioligand (K$_D$ value: 0.59±0.07 nM).

Results and Discussion.

In Table I the results are shown for the inhibition by the various NBTI derivatives of the equilibrium binding of [$^3$H]NBTI to human erythrocytes.

The aim of the first series of modifications was conversion of the 4-nitrobenzyl group on NBTI to a substituent with a lower hydrophilicity. The oxadiazole functionality instead of a nitro group in compounds 14-16 showed high activity, comparable to NBTI itself. This ring system was then systematically modified to yield 2,1-isoxazole (compounds 23 and 24), 2,1-isothiazole (compounds 28 and 31), imidazole (37, 38) and thiazole (41) derivatives, respectively.

Compound 23 showed reduced activity compared to 14. Apparently, replacement of one N with C as in compound 23 is not very favorable, although such manipulation substantially decreases the compound's hydrophilicity. In a further effort to reduce polarity, S was introduced instead of O in the isoxazole ring to produce isothiazole 28. Also this compound showed a decline in affinity, with both compounds displaying $K_i$ values of approx. 100 nM.

Further modification of the oxadiazole functionalities in 14 and 15 to imidazoles (37 and 38) had a negative effect on affinity. The free NH group in the imidazole group may have a profound effect on the compound's basicity. Therefore, thiazole 41 with S instead of NH was prepared. This substantially less polar derivative had appreciable affinity for the nucleoside transport protein ($K_i$=165 nM), although quite comparable to imidazole derivative 37.

In the C6-substituted compounds we also studied the effect of the position of substitution with respect to the —SCH2— bridge between nucleobase and ring substituent (pairs of compounds 14-15,23-24 and 37-38). All 'ortho' substituted nucleosides (15,24 and 38) showed a reduced affinity when compared to their counterparts. A similar conclusion was drawn in another study in which the nitro functionality was shifted from the para position to other positions in the ring. (Paul, B.; Chen, M. F.; Paterson, A. R. P. J. Med. Chem. 1975, 18, 968-973). Further modification of compound 15 by introduction of chlorine in the benzyl ring system did not improve the binding affinity in 16. An analogous approach, bromination of 28 to yield 31, resulted in a 2.6-fold affinity gain from 108 to 42 nM.

Next the effect of N9 substitution was studied. Since the ribose group with three hydroxyl groups is very hydrophilic, the N9 position was substituted with different alkyl and modified alkyl groups. Introduction of a hydroxyl group at C4 in a butyl substituent (47) had a negative effect on the binding affinity, whereas the protected alcohol showed a higher affinity (46). Compound 48 with a cyclopentyl group on N9 showed a decrease in activity compared to a simple n-butyl substituent (53). Compounds 43 and 44 bearing a tetrahydrofuran and tetrahydropyran N9-substituent, respectively, were designed as deoxy sugar analogs. They also showed a decrease in activity compared to compound 53 with the n-butyl substituent. From these data an n-butyl at N9 was chosen as a less polar substituent, although the ribose group itself (as in NBTI) led to much higher affinity. This became further apparent when synthesizing 54-56, since in all cases a substantial reduction in affinity (16-577-fold) was observed when compared to the ribose-substituted analogs. This huge decrease in affinity had not been observed when comparing similar series of compounds on the actual transport in intact erythrocytes. In this typical assay the compounds need to enter the cells first, which is more easily achieved with the N9-butyl derivatives. Differences in activity were negligible in this case. (Paul, B.; Chen, M. F.; Paterson, A. R. P. J. Med. Chem. 1975, 18, 968-973).

Finally in case of substitution of N1 with a carbon atom (1-deazapurines) the resulting nucleosides show a decrease in affinity (compound 60 and 61 vs NBTI). Introduction of a nitro group in nucleoside 61 increased the affinity approx. tenfold relative to 60.

TABLE 1

Affinities of novel NBTI analogs for the nucleoside transport protein on human erythrocyte membranes

| Compound | R | R' | X | Y | $K_i$(nM) |
|---|---|---|---|---|---|
| 14 | 4-methylbenzofurazan | ribose | N | H | 1.5(±0.1) |
| 15 | 7-methylbenzofurazan | ribose | N | H | 9.7(±0.2) |
| 16 | 4-chloro-7-methylbenzofurazan | ribose | N | H | 25(±2) |
| 23 | 5-methylbenzisoxazole | ribose | N | H | 96(±1) |
| 24 | 7-methylbenzisoxazole | ribose | N | H | 666(±47) |
| 28 | 5-methylbenzisothiazole | ribose | N | H | 108(±2) |
| 31 | 3-bromo-5-methylbenzisothiazole | ribose | N | H | 42(±4) |
| 37 | 5-methylbenzimidazole | ribose | N | H | 191(±12) |
| 38 | 7-methylbenzimidazole | ribose | N | H | 42%* |

TABLE 1-continued

Affinities of novel NBTI analogs for the nucleoside transport protein on human erythrocyte membranes

| Compound | R | R' | X | Y | $K_i$(nM) |
|---|---|---|---|---|---|
| 41 | benzothiazol-2-yl (4-nitrobenzyl shown below row) | ribose | N | H | 165(±16) |
| 43 | 4-nitrobenzyl | THF | N | H | 937(±31) |
| 44 | 4-nitrobenzyl | THP | N | H | 1200(±100) |
| 46 | 4-nitrobenzyl | THP-O-C4 | N | H | 488(±51) |
| 47 | 4-nitrobenzyl | butan-4-ol | N | H | 1140(±40) |
| 48 | 4-nitrobenzyl | cyclopentyl | N | H | 736(±67) |
| 53 | 4-nitrobenzyl | n-butyl | N | H | 238(±38) |
| 54 | benzoxadiazolyl | n-butyl | N | H | 5600(±600) |
| 55 | benzisothiazolyl | n-butyl | N | H | 3100(±200) |
| 56 | bromo-benzisothiazolyl | n-butyl | N | H | 682(±12) |
| 60 | benzyl | ribose | C | Cl | 670(±31) |
| 61 | 4-nitrobenzyl | ribose | C | Cl | 47(±4) |

*Percentage of displacement at concentration of 10 μM

Experimental Section

Chemistry. $^1$H and $^{13}$C NMR spectra were recorded on a Bruker AC-200 instrument. Samples were measured in CDCl$_3$, CD$_3$OD and/or d$_6$-DMSO, with Me$_4$Si as an internal standard; δ in ppm, J in Hz. Thin-layer chromatography (TLC) was performed by using plastic sheets precoated with silica gel 60 F254 (0.2 mm) type E (Merck). Chromatographic spots were visualized by UV light. Column chromatography was conducted on silica gel 60 (0.040-0.063 mm) unless otherwise noted. Melting points (uncorrected) were determined in open glass capillaries on an electrothermal apparatus. Mass spectra and accurate mass measurements were performed using a Finnigan MAT 900 spectrometer equipped with an electrospray interface. All commercial chemicals were used without further purification.

General procedure (A): Coupling of the alkyl bromide with 6 mercaptopurine (riboside). A mixture of 6-mercaptopurine riboside (1 eq.) or 6-mercaptopurine (1 eq.), anhydrous potassium carbonate (1 eq.), and 1.1 equivalents of alkyl bromide in DMF was stirred at room temperature for 30 min to 18 h. The mixture was poured in water and the solution was adjusted to pH=7 with concentrated HCl. The mixture was extracted several times with ethyl acetate and the organic layer was dried (MgSO$_4$), filtered and evaporated. The product was purified by column chromatography eluting with EtOAc/MeOH, or recrystallization.

General method (B): Alkylation of N9 position in purines by Mitsunobu reaction. Diethyl azodicarboxylate (0.05 mL, 0.15 mmol) was added in portions to a mixture of 6-substituted purine (0.15 mmol), triphenyl phosphine (79 mg, 0.3 mmol) and the proper alcohol (0.3 mmol) in dry THF (2.7 mL). The mixture was stirred at 0° C. for 1 hr, and then at room temperature for 10 h. After removal of the solvent in vacuo, the product was separated by flash column chromatography.

General method (C): N9-Substitution of 6-mercaptopurine by tetrahydropyranyl or tetrahydrofuranyl ring. To 60 mL of anhydrous ethyl acetate warmed to 50° C. were added 6-(4-nitrobenzyl)mercaptopurine (1 eq.) and p-toluene-sulfonic acid (0.1 eq.). The mixture was vigorously stirred and 2,3-dihydropyran or 2,3-dihydrofuran (3 eq.) added dropwise. The solution was stirred for 1 hr and cooled to room temperature. Concentrated aqueous ammonia was added and the solution stirred for 5 min. It was extracted twice with water. The ethyl acetate layer was dried over anhydrous sodium sulfate and removed under reduced pressure. Recrystallization from petroleum ether (40-60° C.) gave the product.

General method (D): Coupling of the 6-substituted mercaptopurine with butyl bromide. 6-Substituted mercaptopurine (1 eq.) was suspended in DMF. Sodium hydride (60% dispersion in mineral oil, 1.2 eq.) was added and the mixture was stirred at room temperature for 1 h. under N$_2$ atmosphere. Then butyl bromide (1 eq.) was added and the stirring was continued at room temperature for 18 h. under N$_2$ atmosphere. The reaction mixture was poured into water and extracted with ethyl acetate. The organic layer was dried (K$_2$CO$_3$) and evaporated, to give a mixture of N9- and N7-butylated purines. The product was purified by column chromatography, while eluting with EtOAc/PE. In all cases the first fraction was N9-substituted material.

6-(Benzo[1,2,5]oxadiazol-5-ylmethylsulfanyl-9-O-D-ribofuranosyl-9H-purine (14). This compound was prepared by coupling 6-mercapto purine riboside with bromide 11 (Ghosh, P. B.; Ternai, B.; Whitehouse; M. W. J. Med. Chem. 1972, 15, 255-260 and Ghosh, P. B.; Whitehouse, M. W. J. Med. Chem. 1968, 11, 305-311) by the general method A, in 46% yield. $^1$H NMR (CD$_3$OD): 8.74 (s, 1H), 8.62 (s, 1H), 7.97 (s, 1H,), 7.82 (d, 1H, J=9.51 Hz), 7.62 (dd, 1H, J=8.04, 1.09 Hz), 6.08 (d, 1H, J=5.85 Hz), 4.79 (s, 2H), 4.15 (m, 1H), 4.34 (m, 1H), 3.82 (m, 2H), 4.71 (m, 1H); $^{13}$CNMR (CD$_3$OD): δ 160.80, 152.75, 149.42, 144.84, 144.07, 135.36, 117.37, 115.84, 90.91, 87.70, 75.76, 72.19, 63.01, 33.11; HRMS calc. for C$_{17}$H$_{17}$N$_6$O$_5$S m/z=417.098 (M+H), found 417.1038.

6-(Benzo[1,2,5]oxadiazol-4-ylmethylsulfanyl-9-β-D-ribofuranosyl-9H-purine (15). This compound was prepared by coupling the alkyl bromide 12 (Ghosh, P. B.; Ternai, B.; Whitehouse; M. W. J. Med. Chem. 1972, 15, 255-260 and Ghosh, P. B.; Whitehouse, M. W. J. Med. Chem. 1968, 11, 305-311) with mercaptopurine riboside using general method A, in 78% yield. $^1$H NMR (CD$_3$OD): δ 8.73 (s, 1H), 8.61 (s, 1H), 7.78 (d, 1H, J=8.77 Hz), 7.65 (d, 1H, J=6.58 Hz), 7.43 (dd, 1H, J=8.78, 6.58 Hz), 6.08 (d, 1H, J=5.85 Hz), 5.07(s, 2H), 4.72 (m, 1H), 4.35 (dd, 1H, J=5.12, 3.65 Hz), 4.16 (m, 1H), 3.82 (m, 2H); $^{13}$C NMR (CD$_3$OD): δ 160.5, 156.9, 153.9, 152.6, 146.0, 136.3, 135.2, 133.4, 128.9, 117.4, 90.2, 88.1, 84.2, 76.2, 72.6, 63.6, 30.1. Mp 154-155° C., decomp.; HRMS calc. for C$_{17}$H$_{17}$N$_6$O$_5$S m/z=417.0981 (M+H), found 417.004.

6-(6-Chloro-benzo[1,2,5]oxadiazol-4-ylmethylsulfanyl-9-β-D-ribofuranosyl-9H-purine (16). Coupling the alkyl bromide 13 (Ghosh, P. B.; Ternai, B.; Whitehouse; M. W. J. Med. Chem. 1972, 15, 255-260 and Ghosh, P. B.; Whitehouse, M. W. J. Med. Chem. 1968, 11, 305-311) with mercaptopurine riboside by general method A, gave 16 in 70% yield. $^1$H NMR (CD$_3$OD): δ 8.74 (s, 1H), 8.62 (s, 1H), 7.91 (s, 1H), 7.64 (s, 1H), 6.08 (d, 1H, J=5.85 Hz), 5.07 (s, 2H), 4.72 (dd, 1H, J=5.85, 5.11 Hz), 4.35 (dd, 1H, J=5.12, 3.65 Hz), 4.16 (m, 1H), 3.82 (m, 2H); $^{13}$C NMR (CD$_3$OD): δ 177.40, 151.42, 149.34, 143.58, 137.17, 132.24, 128.93, 113.79, 95.37, 87.84, 85.65, 73.74, 70.15, 61.13, 27.36 and 11.87; Mp: 214-215° C.; HRMS calc. for C$_{17}$H$_{16}$N$_6$O$_5$SCl m/z=451.0591 (M+H), found 451.0572.

6-(Benzo[c]isoxazol-5-ylmethylsulfanyl-9-O-D-ribofuranosyl-9H-purine (23). Coupling of 21 (Phillips, B. T.; Hartman, G. D. J. Heterocyclic Chem. 1986, 23, 897-899) with mercaptopurine riboside was performed by general method A. The product was formed in 54% yield. $^1$H NMR (CD$_3$OD): δ 9.36 (s, 1H), 8.72 (s, 1H), 8.59 (s, 1H), 7.75(s, 1H), 7.75 (d, 1H, J=2.9 Hz), 7.51 (d, 1H, J=2.9 Hz), 6.06 (d, 1H, J=5.1 Hz), 4.70 (s, 2H), 4.35 (dd, 1H, J=5.1, 5.9 Hz), 4.28 (m, 1H); 3.91 (m, 1H), 3.86 (m, 2H); $^{13}$C NMR (CD$_3$OD): δ 156.9, 152.4, 144.4, 134.5, 130.2, 129.6, 120.0, 115.4, 113.1, 90.7, 87.5, 75.5, 71.2, 62.8, 33.6; Mp: 213-214° C.; HRMS calc. for C$_{18}$H$_{18}$N$_5$O$_5$S m/z=416.1029 (M+H), found 416.1022.

6-(Benzo[c]isoxazol-7-ylmethylsulfanyl-9-β-D-ribofuranosyl-9H-purine (24). Coupling of bromide 22 (Phillips, B. T.; Hartman, G. D. J. Heterocyclic Chem. 1986, 23, 897-899) with 6-mercaptopurine riboside was achieved by general method A. $^1$H NMR (CD$_3$OD): δ 9.47 (s, 1H), 8.74 (s, 1H), 8.58 (s, 1H), 7.58 (d, 1H, J=8.8 Hz), 7.52 (d, 1H, J=6.6 Hz), 6.99 (dd, 1H, J=8.8, 6.6 Hz), 6.07 (d, 1H, J=5.8 Hz), 4.96 (s, 2H), 4.71 (dd, 1H, J=5.3, 4.5 Hz), 4.32 (m, 1H); 4.14 (m, 1H); 3.89-3.72 (m, 2H); $^{13}$C NMR (d$_6$-DMSO): δ 157.8, 152.72, 144.60, 131.80, 125.69, 120.56, 90.93, 87.74, 75.72, 72.24, 63.07, 29.15; Mp: 200-201° C.; HRMS calc. for C$_{18}$H$_{18}$N$_5$O$_5$S$_2$ m/z=416.1029 (M+H), found 416.1024.

6-(Benzo[c]isothiazol-5-ylmethylsulfanyl-9-β-D-ribofuranosyl-9H-purine (28). This compound was prepared from bromide 27 (Singerman, G. M. J. Heterocyclic Chem 1975, 12, 877-882) (187 mg, 0.82 mmol) and 6-mercaptopurine riboside (214 mg, 0.75 mmol) by general method A. The solvent was decanted from the white precipitate and after washing with water and drying over silica blue in vacuo 28 (81 mg, 25%) was obtained as an off-white solid. $^1$H NMR (d$_6$-DMSO): δ 9.73 (s, 1H), 8.84 (s, 1H), 8.75 (s, 1H), 8.00 (s, 1H), 7.78 (d, 1H, J=9.5 Hz), 7.59 (d, 1H, J=9.5 Hz), 6.03 (d, 1H, J=5.1 Hz), 5.30(broad, 3H, 3×OH), 4.82 (s, 2H), 4.62 (dd, 1H, J=5.1, 5.9 Hz), 4.20 (m, 1H); 3.99 (m, 1H), 3.66 (m, 2H); $^{13}$C NMR (d$_6$-DMSO): δ 160.4, 158.9, 151.5, 148.3, 147.0, 143.4, 134.1, 133.6, 131.1, 130.6, 121.8, 121.3, 87.8, 85.7, 74.0, 70.2, 61.2, 31.6; Mp: 183-186° C.; HRMS calc. for C$_{18}$H$_{18}$N$_5$O$_4$S$_2$ m/z=432.0800 (M+H), found 432.0835.

3-Bromo-5-methyl-2,1-benzisothiazole (29). To a solution of compound 26 (Singerman, G. M. J. Heterocyclic Chem 1975, 12, 877-882) (1.49 g, 10.0 mmol) in dry THF (50 ml) at −80° C. was added n-BuLi (11.2 mmol, 7.0 ml of a 1.6 M solution in n-hexane) dropwise. The black solution was stirred at −75° C. for 20 min after which bromine (1.0 ml, 19.9 mmol) was added. The mixture was slowly warmed to room temperature and poured into a 1 N HCl (100 mL) solution. Extraction with diethyl ether (3×50 ml), drying (MgSO$_4$), evaporation of the solvent and purification by silicagel column chromatography (petroleum ether (40-60)/EtOAc=95/5) gave 29 (1.55 g, 68%) as a red oil. $^1$H NMR (CDCl$_3$): δ 7.66 (d, 1H, J=9.5 Hz), 7.33 (d, 1H, J=9.5 Hz), 7.30 (s, 1H), 2.46 (s, 3H); $^{13}$C NMR (CDCl$_3$): δ 160.1, 134.6, 134.1, 131.8, 130.0, 121.2, 118.0, 21.3.

3-Bromo-5-bromomethyl-2,1-benzisothiazole (30). This compound was prepared as 11 by benzylic bromination in the presence of N-bromosuccinimide (Ghosh, P. B.; Ternai, B.; Whitehouse; M. W. J. Med. Chem. 1972, 15, 255-260 and Ghosh, P. B.; Whitehouse, M. W. J. Med. Chem. 1968, 11, 305-311) in 84% yield. $^1$H NMR (CDCl$_3$): δ 4.61 (s, 2H); 7.49 (d, 1H, J=9.5 Hz); 7.61 (s, 1H); 7.78 (d, 1H, J=9.5 Hz); $^{13}$C NMR (CDCl$_3$): δ 160.9, 134.8, 134.0, 133.2, 130.7, 122.9, 120.0, 33.2.

6-(3-Bromo-benzo[c]isothiazol-5-ylmethyl sulfanyl-9-β-D-ribofuranosyl-9H-purine (31). This compound was prepared from bromide 30 (169 mg, 0.55 mmol) and 6-mercaptopurine riboside (141 mg, 0.50 mmol) by general method A in 86% yield as a white solid. $^1$H NMR (d$_6$-DMSO): δ 8.85 (s, 1H), 8.76 (s, 1H), 7.67 (d, 1H, J=9.5 Hz); 7.79 (m, 2H), 6.03 (d, 1H, J=5.5 Hz), 5.34 (b, m, 3H), 4.87 (s, 2H), 4.62 (dd, 1H, J=5.1, 5.5 Hz), 4.21 (m, 1H), 4.00 (m, 1H), 3.69 (m, 2H); $^{13}$C NMR (d$_6$-DMSO) δ 160.4, 158.7, 151.5, 148.4, 143.5, 135.7, 133.8, 132.8, 131.6, 131.1, 122.0, 119.6, 87.9, 85.7, 73.8, 70.2, 61.2, 31.3; Mp: 129-131° C.; HRMS calc. for C$_{18}$H$_{17}$BrN$_5$O$_4$S$_2$ m/Z=509.9905 (M+H), found 509.9918.

(Benzimidazol-5-yl)-methanol (34). To a suspension of LiAlH$_4$ (2.393 g, 63.15 mmol) in 73 mL of dry THF was added dropwise a solution of ester 32 (Sun, Q.; Gatto, B.; Yu, C.; Liu, A.; Liu, L. F.; LaVoie, E. J. J. Med. Chem. 1995, 38, 3638-3644) (4.0 g, 21.05 mmol) in 22 mL of dry THF. The mixture was refluxed. The excess of LiAlH$_4$ was destroyed cautiously by a saturated solution of NH$_4$Cl. The organic layer was removed and the water layer was extracted with ethyl acetate. The organic extract was dried (K$_2$CO$_3$) and evaporated to give 34 as a yellow oil that crystallized spontaneously (Yield 70%). $^1$H NMR (CD$_3$OD): δ 8.13 (s, 1H), 7.61 (s, 1H), 7.57 (d, 1H, J=8.04 Hz), 7.26 (d, 1H, J=8.77 Hz), 5.07 (s, 2H).

6-(3-H-Benzimidazol-5-yl)methylsulfanyl-9-β-D-ribofuranosyl-9H-purine (37). (Cyanomethyl)trimethyl-phosphonium iodide 36 (299 mg, 1.23 mmol) was added to a mixture of alcohol 35 (200 mg, 1.35 mmol), 6-mercaptopurine riboside (284 mg, 1.00 mmol), and DIPEA (0.25 mL) in propionitrile (3 mL). The mixture was heated at 90° C. and some drops of DMF were added to obtain a clear solution. The mixture was stirred overnight at 90° C., cooled to room temperature and water was added. Upon standing at room temperature, 37 was formed as a pale brown precipitate collected by filtration and dried in vacuo (65% yield). $^1$H NMR (d$_6$-DMSO): δ 8.83, 8.72 (2×s, 2H), 8.21 (s, 1H), 7.70 (s, 1H), 7.54 (d, 1H, J=8.04 Hz), 7.31 (d, 1H, J=8.04 Hz), 6.01 (d, 1H, J=5.85 Hz), 5.57 (d, 1H, J=5.85 Hz), 5.27 (d, 1H, J=5.11 Hz), 5.16 (m, 1H), 4.81 (s, 2H), 4.62 (m, 1H), 4.19 (m, 2H), 3.99 (m, 1H); $^{13}$C NMR (d$_6$-DMSO): δ 162.0, 152.8, 149.5, 144.5, 133.7, 132.6, 125.2, 90.5, 87.6, 75.7, 72.2, 63.0, 33.9; Mp: 196-198° C.; HRMS calc. for C$_{18}$H$_{19}$N$_6$O$_4$S m/z=415.1200 (M+H), found 415.1155.

(Benzimidazol-4-yl)methanol (35). The same reduction reaction as for ester 32 was performed on ester 33; in this case the yield was 88%. $^1$H NMR (CD$_3$OD): δ 8.15 (s, 1H), 7.53 (m, 1H), 7.24 (m, 2H), 4.98 (s, 2H).

6-(3-H-Benzimidazol-4-yl)methylsulfanyl-9-O-D-ribofuranosyl-9H-purine (38). Starting from alcohol 35 and the same reaction condition as 37 gave the coupled product 38 in 44% yield. $^1$H NMR (CD$_3$OD): δ 8.76, 8.58 (2×s, 2H), 8.20 (s, 1H), 7.54(m, 1H), 7.41 (d, 1H, J=7.31 Hz), 7.20 (m, 1H), 6.08 (d, 1H, J=5.84 Hz), 5.03 (s, 2H), 4.72 (m, 1H), 4.35 (m, 1H), 4.15 (m, 2H), 3.83 (m, 1H); Mp=decomp. 136-138° C.;

13C-NMR=Sent to NMR-Department

MS: Sent to Mass-Department.

(Benzothiazol-6-yl)-methanol (40). To a suspension of 76 mg of LiAlH$_4$ in dry THF (20 mL) under N$_2$ was added dropwise and at 0° C. a solution of ester 39 (207 mg, 1 mmol) in dry THF (6.7 ml). After 2 h. the ice bath was removed and the mixture was stirred overnight at room temperature, then cooled to 0° C. The excess of LiAlH$_4$ was destroyed very cautiously by a saturated solution of NH$_4$Cl. The organic layer was removed and the aqueous layer was extracted with EtOAc. The combined organic extracts were dried (Na$_2$CO$_3$) and evaporated, obtaining an orange oil that was purified by column chromatography, eluting with EtOAc/MeOH (90/10). $^1$H NMR (CD$_3$OD): δ 9.20 (s, 1H), 8.02 (m, 2H), 7.53 (d, 1H, J=8.04 Hz), 4.76 (s, 2H).

6-(Benzothiazol-6-yl)methylsulfanyl-9-(β-D-ribofuranosyl)purine (41). (Cyanomethyl)trimethylphosphonium iodide (45 mg) was added to a mixture of 40 (Burger, A.; Sawhney, S. N. J. Med. Chem. 1968, 11, 270-273) (33 mg, 0.2 mmol), 6-mercaptopurine riboside (42 mg, 0.2 mmol) and DIPEA (0.04 ml) in 0.43 ml of propionitrile. The mixture was heated at 90° C. and few drops of DMF were added to obtain a clear solution. Stirring was continued overnight at 90° C. The mixture was cooled to room temperature, water was added and slowly a pale brown precipitate was formed. The solid was collected and dried under vacuum. $^1$H NMR (CD$_3$OD): δ9.20, 8.74 (2×s, 2H), 8.59 (s, 1), 8.18 (s, 1H), 7.98 (d, 1H, J=8.78 Hz), 7.67 (d, 1H, J=8.77 Hz), 6.07 (d, 1H, J=5.11 Hz), 4.84 (s, 2H), 4.72 (m, 1H), 4.35 (m, 1H), 4.17 (m, 2H), 3.83 (m, 1H);$^{13}$C-NMR (CDCl$_3$/d6-DMSO): 6161.5, 157.1, 153.5, 152.8, 149.5, 144.6, 137.4, 135.2, 129.0, 124.0, 123.7, 90.6, 87.6, 75.7, 72.2, 63.0, 33.2, 19.4; Mp=decomp. 140° C.; HRMS calc. for C$_{18}$H$_{18}$N$_5$O$_4$S$_2$ m/Z=432.5100 (M+H), found 432.0787.

6-(4-Nitrobenzylsulfanyl)-9-(tetrahydro-furan-2-yl)-9H-purine (43). This compound was prepared from 42 by general method C in 67% yield. $^1$H NMR (CDCl$_3$): δ 8.75 (s, 1H), 8.15 (s, 1H), 7.62 (d, 1H, J=8.9 Hz), 5.52 (d, 1H, J=8.9 Hz), 4.75 (m, 1H), 4.44 (m, 2H), 2.19 (m, 2H); $^{13}$CNMR (CDCl$_3$): δ 158.59, 151.17, 148.46, 145.88, 141.217, 129.89, 128.58, 127.88, 126.54, 123.11, 121.12, 97.14, 64.79, 61.25, 56.12, 32.111, 23.15; HRMS calc for C$_{16}$H$_{166}$N$_5$O$_3$S m/z=358.3919 (M+H), found 358.3911.

6-(4-Nitrobenzylsulfanyl)-9-(tetrahydro-pyran-2-yl)-9H-purine (44). This compound was obtained from 42 by general method A in 62% yield. $^1$H NMR (CDCl$_3$): δ 8.74 (s, 1H), 8.18 (d, 1H, J=9.2 Hz), 8.13 (s, 1H), 7.65 (d, 1H, J=9.2 Hz), 5.74 (m, 1H), 4.72 (s, 2H), 4.15 (m, 2H), 3.78 (m, 3H), 2.29 (m, 3H); $^{13}$C NMR (CDCl$_3$): δ 158.59, 151.13, 148.43, 145.64, 141.21, 129.72, 128.08, 127.02, 126.65, 123.35, 121.47, 97.93, 64.64; HRMS calc. for C$_{17}$H$_{18}$N$_5$O$_3$S m/z=372.1131 (M+H), found 372.1104.

6-(4-Nitrobenzylsulfanyl)-9-purine-9-yl)-butan-1-ol (47). Compound 46 was made from 42 by general method B in 86% yield. $^1$H NMR (CDCl$_3$): δ 8.65 (s, 1H), 8.05 (d, 1H, J=9.2 Hz), 7.97 (s, 1H), 7.70 (d, 1H, J=9.2 Hz), 4.65 (s, 2H), 4.42 (m, 1H), 4.21 (m, 3H), 3.72 (m, 3H), 3.33 (m, 3H), 2.12 (m, 3H), 1.51 (m, 4H).

Deprotection of 46 was done with p-toluene sulfonic acid to give 47 in 65% yield. $^1$H NMR (CDCl$_3$): δ 8.70 (s, 1H), 8.36 (s, 1H), 8.10 (d, 1H, J=9.2 Hz), 7.70 (d, 1H, J=9.2 Hz), 4.74 (s, 2H), 4.43 (m, 2H), 4.57 (m, 2H), 1.97 (m, 2H), 1.51 (m, 2H); $^{13}$C NMR (CDCl$_3$): δ 159.22, 151.71, 148.89, 147.15, 145.77, 143.02, 132.14, 131.94, 129.98, 128.56, 123.68, 62.09, 43.95, 31.81, 29.19, 26.98; Mp: 128-130° C.; HRMS calc. for C$_{16}$H$_{19}$N$_5$O$_3$S m/z=360.1130 (M+H), found 360.1123.

6-(4-Nitrobenzylsulfanyl)-9-cyclopentyl-9H-purine (48). This compound was obtained from 42 by method B in 56% yield. $^1$H NMR (CD$_3$OD): δ 8.73 (s, 1H), 8.16 (d, 1H, J=9.2 Hz), 8.14 (s, 1H), 7.65 (d, 1H, J=9.2 Hz), 4.96 (m, 1H), 4.72 (s, 2H), 4.12 (m, 1H), 2.29 (m, 2H), 1.97-1.80 (m, 3H); $^{13}$C NMR (CDCl$_3$): δ 158.60, 151.13, 148.43, 145.64, 141.21, 129.72, 126.66, 123.35, 56.09, 32.31, 31.04, 23.55; Mp: 92-94° C.; HRMS calc. for C$_{17}$H$_{18}$N$_5$O$_2$S m/z=356.1181 (M+H), found 356.1179.

9-Butyl-6-(4-nitrobenzylsulfanyl)-9H-purine (53). This compound was made by general method A from 42 in 98% yield. $^1$H NMR (d$_6$-DMSO): 68.76 (s, 1H), 8.52 (s, 1H), 8.18 (d, J=8.77 Hz), 7.76 (d, J=8.77 Hz), 4.79 (s, 2H), 4.25 (t, 2H, J=7.31 Hz), 1.82 (tt, 2H, J=7.31 Hz), 1.24 (tq, 2H, J=7.31 Hz), 0.89 (t, 3H, J=7.31 Hz); $^{13}$C NMR, HRMS calc. for C$_{16}$H$_{18}$N$_5$O$_2$S m/z=344.1181 (M+H), found 344.1148.

6-(Benzo[1,2,5]oxadiazol-4-ylmethylsulfanyl-9H-purine (50). This compound was prepared by general method A, from 49 and bromide 12 in 88% yield. $^1$H NMR (CD$_3$OD): δ 8.77 (s, 1H), 8.13 (s, 1H), 7.72 (d, 1H, J=8.77 Hz), 7.57 (d, 1H, J=6.58 Hz), 7.32 (dd, 1H, J=8.77, 5.84 Hz), 5.07 (s, 2H).

6-(Benzo[1,2,5]oxadiazol-4-ylmethylsulfanyl-purine-9-yl-butane (54). This compound was made by general method D from 50 and butyl bromide in 63% yield. $^1$H NMR (CD$_3$OD): δ 8.76 (s, 1H), 7.93 (s, 1H), 7.63 (d, 1H, J=8.77 Hz), 7.52 (d, 1H, J=6.58 Hz), 7.26 (dd, 1H, J=6.58, 8.78 Hz), 4.97 (s, 2H), 4.20 (t, 2H, J=7.31 Hz), 1.83 (t, 2H, J=7.31 Hz), 1.28 (t, 2H, J=7.31 Hz), 0.89 (t, 3H, J=7.31 Hz); $^{13}$C NMR (CDCl$_3$): δ 151.49, 145.61, 142.67, 129.75, 123.38, 121.32, 98.08, 43.60, 31.71, 31.43, 19.58, 13.21; HRMS calc. for C$_{16}$H$_{17}$N$_6$OS (M+H), 341.42 found 341.1184.

6-(Benzo-2,1-isothiazol-5-yl)methylsulfanyl-9-butyl-9H-purine (55). This compound was made by stirring a mixture of 55 (315 mg, 1.38 mmol), 6-mercaptopurine (245 mg, 1.55 mmol) and K$_2$CO$_3$ (228 mg, 1.65 mmol) in DMF (5 mL) at room temperature for 3 h. (general method A). After addition of water (30 ml) the mixture was allowed to stand at 5° C. for 4 days. An oily residue separated from the water layer. After removal of the water layer, toluene (20 ml) was added and evaporated in vacuo. This procedure was repeated twice after which the remaining residue was dissolved in DMF (10 ml). At 0° C. NaH (60% dispersion in mineral oil, 70 mg, 1.75 mmol) was added. After 30 min n-butylbromide (200 ml, 1.85 mmol) was added. The reaction was stirred overnight at room temperature and poured into water (40 ml). Extraction with EtOAc (3×20 ml), drying (MgSO$_4$) and concentration in vacuo gave an orange oil that was purified by silicagel column chromatography (n-heptane/EtOAc=2/1) to afford 55 (245 mg, 50%) as a white solid. $^1$H NMR (CDCl$_3$): δ 9.11 (s, 1H), 8.77 (s, 1H), 7.95 (s, 1H), 7.86 (s, 1H), 7.79 (d, 1H, J=9.5 Hz), 7.55 (d, 1H, J=9.5 Hz), 4.77 (s, 2H), 4.28 (t, 2H, J=6.6 Hz), 1.89 (m, 2H), 1.33 (m, 2H), 0.95 (t, 3H, J=7.3 Hz); $^{13}$C NMR (CDCl$_3$): δ 160.6, 159.5, 151.4, 148.4, 143.9, 142.6, 134.2, 133.5, 130.9, 130.3, 121.4, 121.2, 43.4, 32.3, 31.6, 19.5, 13.1; Mp: 93-94° C.; HRMS calc. for $C_{17}H_{17}N_5BrS_2$ m/z=434.0109 (M+H), found 434.0080.

6-(3-Bromo-benzo-2,1-isothiazol-5-yl)methylsulfanyl-9H-purine (52). This compound was made by general method A, from bromide 30 in 90% yield as a white solid. $^1$H NMR ($d_6$-DMSO): δ 8.79 (s, 1H), 8.48 (s, 1H), 7.79 (m, 2H), 7.67 (d, 1H, J=9.5 Hz), 4.85 (s, 2H), 3.33 (b, s, 1H, NH); $^{13}$C NMR ($d_6$-DMSO) δ 160.3, 156.9, 151.3, 150.6, 143.7, 135.9, 133.8, 132.7, 131.7, 129.2, 122.0, 119.5, 31.3.

6-(3-Bromo-benzo[c]isothiazol-5-yl)methylsulfanyl-purine-9-yl-butane (56). This compound was prepared by the general method D from 52 and n-butylbromide in 69% yield. $^1$H NMR (CDCl$_3$): δ 8.78 (s, 1H), 7.95 (s, 1H), 7.71 (m, 2H), 7.57 (d, 1H, J=9.5 Hz), 4.78 (s, 2H), 4.25 (t, 2H, J=6.6 Hz), 1.89 (m, 2H), 1.34 (m, 2H), 0.96 (t, 3H, J=7.3 Hz); $^{13}$C NMR (CDCl$_3$): δ 160.7, 159.3, 151.4, 148.5, 142.6, 134.9, 134.0, 131.9, 131.1, 130.9, 122.1, 119.7, 43.5, 32.3, 31.7, 19.6, 13.2; Mp: 118-119° C.; HRMS calc for $C_{17}H_{18}N_5S_2$ ml/Z 356.1003 (M+H), found 356.0927.

5-Chloro-7-benzylsulfanyl-3-β-D-ribofuranosyl-3H-imidazo[4,5-b]pyridine (60). A mixture of 57 (0.1662 g, 0.37 mmol), benzylthiol (0.065 g, 0.6 mmol) and 0.02 mL of Et$_3$N in 2 mL of DMF was stirred at room temperature for 18 h. under N$_2$ atmosphere. The solution was extracted with ether, dried and purified by flash chromatography (PE/EA, 1:1), yielding 5-chloro-7-(benzylsulfanyl)-3-(2', 3', 5'-tri-O-acetyl-β-D-ribofuranosyl)-3H-imidazo[4,5-b]pyridine 58 (168 mg) in 85% yield. $^1$H NMR (CDCl$_3$): δ 8.13 (s, 1H), 7.42-7.31 (m, 5H), 7.08 (s, 1H), 6.23 (d, 1H, J=5.1 Hz), 5.85 (dd, 1H, J=5.1, 5.9 Hz), 5.65 (dd, 1H, J=5.1, 5.9 Hz), 4.43 (s, 2H), 4.38 (m, 2H), 2.28, 2.12, 1.90 (3×s, 3H).

Deprotection of 58 with a saturated solution of ammonia in methanol at 0° C. for 18 h. gave 83 mg of 60 (65%). $^1$H NMR (CD$_3$OD): δ 8.60 (s, 1H), 7.40-7.29 (m, 5H), 7.25 (s, 1H), 6.04 (d, 1H, J=5.1 Hz), 4.69 (dd, 1H, J=5.1, 5.9 Hz), 4.43 (s, 2H), 4.36 (dd, 1H, J=5.1, 5.9 Hz), 4.15(m, 1H), 3.94-3.80 (m, 2H); $^{13}$C NMR (CD$_3$OD): 8147.15, 145.80, 145.101, 144.324, 137.180, 130.02, 129.81, 128.53, 126.77, 115.19, 90.65, 87.17, 75.19, 71.82, 62.75, 35.70; Mp: 154-156° C.; HRMS calc. for $C_{18}H_{19}N_3O_4SCl$ m/z=408.0784 (M+H), found 408.0678.

5-Chloro-7-(4-nitro-benzylsulfanyl)-3-β-D-ribofuranosyl-3H-imidazo[4,5-b]pyridine (61). A mixture of 57 (75 mg, 0.17 mmol), p-nitro-benzylthiol (0.85 g, 0.5 mmol) and 0.1 mL of Et$_3$N in 5 mL of DMF was stirred at room temperature for 18 h. under N$_2$ atmosphere. The solution was extracted with ether, dried and purified by flash chromatography (PE/EA. 1:1), yielding 72 mg of 5-chloro-7-(4-nitrobenzylsulfanyl)-3-(2', 3', 5'-tri-O-acetyl-β-D-ribofurano-syl)-3H-imidazo[4,5-b]pyridine 59 (75%). $^1$H NMR (CDCl$_3$): δ 8.19 (d, 2H, J=8.0), 8.15(s, 1H), 7.60 (s, 1H), 755 (d, 2H, J=8.0, 2H), 6.21 (d, 1H, J=5.1 Hz), 5.83 (dd, 1H, J=5.1, 5.9 Hz), 5.64 (dd, 1H, J=5.1, 5.9 Hz), 4.63 (s, 2H), 4.38 (m, 2H), 2.14, 2.12, 2.08 (3×s, 3H). Deprotection of 59 with saturated solution of ammonia in methanol at 0° C. for 18 h, gave 50 mg 61 (88%). $^1$H NMR (CDCl$_3$): δ 8.74 (s, 1H), 8.14 (d, 2H, J=8.0), 7.66 (d, 2H, J=8.0, 2H), 7.18 (s, 1H), 6.03 (d, 1H, J=5.1 Hz), 4.89 (s, 2H), 4.69 (dd, 1H, J=5.1, 5.9 Hz), 4.43 (m 1H), 3.88-3.78 (m, 2H). $^{13}$C NMR (CD$_3$OD): 147.15, 145.80, 145.101, 144.324, 137.180, 130.02, 129.78, 128.75, 115.495, 90.91, 87.49, 75.46, 72.16, 63.13, 36.07; Mp: 162-165° C.; HRMS calc. for $C_{18}H_{18}N_4O_6ClS$ m/z=453.0635 (M+H), found 453.0614.

Erythrocytes and membrane preparation. Whole human blood (Blood Bank, Leiden University Medical Center) was stirred in lysis buffer (½ v/v, 10 mM MgCl$_2$ in 10 mM Tris HCl, pH 8.0 at 25° C.) for 1 h. After homogenization it was centrifuged for 50 min at 19,000 rpm. The supernatant was removed and the pellet was dissolved in ice-cold water and centrifuged again for 50 min. This procedure was repeated two more times. After removal of the last supernatant 25 mL of buffer (50 mM Tris HCl, pH 7.4 at 25° C.) was added to the final pink pellet. This suspension was homogenized and the ghosts were collected. Aliquots were stored at −80° C. until further use.

[$^3$H]NBTI binding assay. Saturation and displacement equilibrium NBTI binding to membranes prepared from human erythrocytes (ghosts) was determined at 25° C. based on a method previously described. (I Jzerman, A. P.; Voorschuur, A. H. Naunyn-Schmiedeberg's Arch Pharmacol 1990, 342, 336-341 (and refs therein)).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

LITERATURE i) Plagemann, P. G. W.; Wohlhueter, R. M.; Woffendin, C. Biochim Biophys Acta 1988, 947, 405-443.

ii) Thorn, J. A.; Jarvis, S. M. Gen. Pharmac. 1996, 27, 613-620.

iii) I Jzerman, A. P.; Voorschuur, A. H. Naunyn-Schmiedeberg's Arch Pharmacol 1990, 342, 336-341 (and refs there in).

iv) Paul, B.; Chen, M. F.; Paterson, A. R. P. J. Med. Chem. 1975, 18, 968-973.

v) Baldwin, S. A.; Mackey, J. R.; Cass, C. E.; Young, J. D. Molecular Medicine Today 1999, 5, 216-224.

vi) Johnston, T. P.; Holum, L. B.; Momtgomery, J. A. J. Amer. Chem. Soc. 1985, 80, 6265-6272.

vii) a) Ghosh, P. B.; Ternai, B.; Whitehouse; M. W. J. Med. Chem. 1972, 15, 255-260. b) Ghosh, P. B.; Whitehouse, M. W. J. Med. Chem. 1968, 11, 305-311.

viii) Temple, C.; Kussner, C. L.; Montgomery, J. A. J. Org. Chem. 1968, 11, 41-43.

ix) Phillips, B. T.; Hartman, G. D. J. Heterocyclic Chem. 1986, 23, 897-899.

x) Singerman, G. M. J. Heterocyclic Chem 1975, 12, 877-882.

xi) a) Zaragoza, F. Tetrahedron 2001, 57, 5451-5454. b) Zaragoza, F.; Stephensen, H. J. Org. Chem. 2001, 66, 2518-2521 xii) Kimura, T.; Takase, Y.; Hayashi, K.; Tanaka, H.; Ohtsuka, I.; Saeki, T.; Kogushi, M.; Yamada, T.; Fujimori, T.; Saitou, I.; Akasaka, K. J. Med. Chem. 1993, 36, 1630-1640.

xiii) Sun, Q.; Gatto, B.; Yu, C.; Liu, A.; Liu, L. F.; LaVoie, E. J. J. Med. Chem. 1995, 38, 3638-3644.

xiv) Burger, A.; Sawhney, S. N. J. Med. Chem. 1968, 11, 270-273.

xv) Yadagiri, B.; Lown, J. W. Synth. Commun. 1990, 20, 955-963.

xvi) Robins, R. K.; Godefroi, E. F.; Taylor, E. C.; Lewis, R. L; Jackson, A. J. Am. Chem. Soc. 1960, 83, 2574-79.

xvii) Toyota, A.; Katagiri, N.; Kaneko, C. Synth. Commun. 1993, 23, 1295-1305.

xviii) De Vries, E. F. J.; Steenwinkel, P.; Brussee, J.; Kruse, C. G.; Van der Gen, J. Org. Chem. 1993, 58, 4315-4325.

xix) Cristalli, G.; Grifantini, M.; Vittori, S. Nucleosides & Nucleotides 1985, 4, 621-639.

xx) Jarvis, S. M. Mol. Pharmacol. 1986, 30, 659-665.

What is claimed is:

1. A thioinosine compound corresponding to formula I

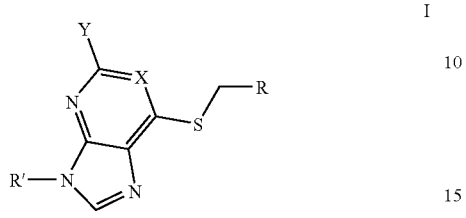

wherein

X is N;

Y is selected from H, OH, SH, F, Cl, Br, I, —CF$_3$, —CHF$_2$, —CH$_2$F, —OCH$_3$, —OC$_2$H$_5$, —CH$_3$, —C$_2$H$_5$;

R is phenyl condensed with a heteroaryl, unsubstituted or mono- or multisubstituted with F, Cl, Br, I, —CF$_3$, —OCH$_3$, —OC$_2$H$_5$, —CH$_3$ or —C$_2$H$_5$;

R' is selected from ribose, mono- or multisubstituted or unsubstituted; C$_{1-6}$-alkyl saturated or C$_{2-6}$-alkenyl unsaturated, mono- or multisubstituted or unsubstituted; C$_{3-8}$-cycloalkyl or C$_{3-8}$-cycloalkyl interrupted by 1 or 2 heteroatoms selected from S, O or N in the ring, mono- or multisubstituted or unsubstituted respectively; phenyl or benzyl, mono- or multisubstituted or unsubstituted respectively; or C$_{1-6}$-alkyl-O—R" or C$_{2-6}$-alkenyl-O—R" with alkyl saturated or alkenyl unsaturated, and mono- or multisubstituted or unsubstituted and R" selected from phenyl, heteroaryl, C$_{3-8}$-cycloalkyl or C$_{3-8}$-cycloalkyl interrupted by 1 or 2 heteroatoms selected from S, O or N in the ring, mono- or multisubstituted or unsubstituted respectively or a salt thereof with a physiologically tolerated acid.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein R is selected from phenyl condensed with a heteroaryl, which is mono- or disubstituted with F, Cl, Br, I, —CF$_3$, —OCH$_3$, —OC$_2$H$_5$, —CH$_3$ or —C$_2$H$_5$.

7. The compound of claim 1, wherein R is selected from phenyl, unsubstituted or monosubstituted with Cl, condensed with =N—O—N=, =N—O—CH=, =N—S—CH=, =N—S—CBr=, —N=CH—NH— or —N=CH—S— wherein phenyl condensed with =N—O—N= refers to:

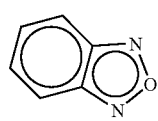

wherein phenyl condensed with =N—O—CH= refers to:

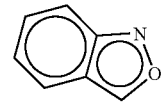

wherein phenyl condensed with =N—S—CH= refers to:

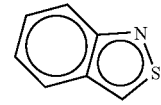

and wherein phenyl condensed with =N—S—CBr= refers to:

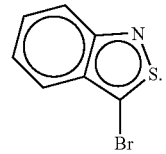

8. The compound of claim 1, wherein R' is selected from ribose, mono- or multisubstituted or unsubstituted;

C$_{1-6}$-alkyl saturated or C$_{2-6}$-alkeny unsaturated, mono- or multisubstituted or unsubstituted;

C$_{3-8}$-cycloalkyl or C$_{3-8}$-cycloalkyl containing 1 or 2 heteroatoms selected from S, O or N in the ring, mono- or multisubstituted or unsubstituted respectively;

benzyl, mono- or multisubstituted or unsubstituted; or

C$_{4-6}$-alkyl-O—R" with alkyl saturated and unsubstituted and R" selected from C$_{3-8}$-cycloalkyl or C$_{3-8}$-cycloalkyl containing 1 or 2 heteroatoms selected from S, O or N in the ring, mono- or multisubstituted or unsubstituted respectively.

9. The compound of claim 1, wherein R' is selected from ribose, mono- or disubstituted or unsubstituted;

C$_{3-6}$-alkyl, saturated and unsubstituted or substituted with F, Cl, Br, I or OH;

C$_{5-7}$-cycloalkyl or C$_{5-7}$-cycloalkyl containing 1 or 2 heteroatoms selected from S, O or N in the ring, mono- or disubstituted or unsubstituted respectively;

benzyl, mono- or disubstituted or unsubstituted; or

C$_{4-6}$-alkyl-O—R" with alkyl saturated and unsubstituted and R" selected from C$_{3-8}$-cycloalkyl containing 1 or 2 heteroatoms selected from S, O or N in the ring, mono- or disubstituted or unsubstituted respectively.

10. The compound of claim 1, wherein R' is selected from ribose, unsubstituted;

n-butyl or butan-4-ol;

cyclopentyl, tetrahydrofuranyl or tetrahydropyranyl, unsubstituted respectively;

benzyl, unsubstituted or mono- or disubstituted with NO$_2$, F, phenyl, I, Cl, trifluoromethoxy, trifluoromethyl or methoxy; or -butyl-O-tetrahydropyranyl.

11. The compound of claim 1, wherein Y is selected from H or Cl.

12. The compound of claim 1, wherein Y represents Cl.

13. The compound of claim 1, wherein said compound is selected from the group consisting of:

2-[6-(Benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(Benzo[1,2,5]oxadiazol-5-ylmethylsulfanyl)-purin-9-yl]-5-hydroxymethyl-tetrahydro-furan-3,4-diol 2-[6-(Benzo[1,2,5]oxadiazol-4-ylmethylsulfanyl)-purin-9-yl]-5-hydroxymethyl-tetrahydro-furan-3,4-diol 2-[6-(5-Chloro-benzo[1,2,5]oxadiazol-4-ylmethylsulfanyl)-purin-9-yl]-5-hydroxymethyl-tetrahydro-furan-3,4-diol 2-[6-(Benzo[c]isoxazol-5-ylmethylsulfanyl)-purin-9-yl]-5-hydroxymethyl-tetrahydro-furan-3,4-diol 2-[6-(Benzo[c]isoxazol-7-ylmethylsulfanyl)-purin-9-yl]-5-hydroxymethyl-tetrahydro-furan-3,4-diol 2-[6-(Benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(3-Bromo-benzo[c]isothiazol-5-ylmethylsulfanyl)-purin-9-yl]-5-hydroxymethyl-tetrahydro-furan-3,4-diol 2-[6-(3H-Benzoimidazol-5-ylmethylsulfanyl)-purin-9-yl]-5-hydroxymethyl-tetrahydro-furan-3,4-diol 2-[6-(3H-Benzoimidazol-4-ylmethylsulfanyl)-purin-9-yl]-5-hydroxymethyl-tetrahydro-furan-3,4-diol 2-[6-(Benzothiazol-6-ylmethylsulfanyl)-purin-9-yl]-5-hydroxymethyl-tetrahydro-furan-3,4-diol 6-(Benzo[1,2,5]oxadiazol-4-ylmethylsulfanyl)-9-butyl-9H-purine 6-(Benzo[c]isothiazol-5-ylmethylsulfanyl)-9-butyl-9H-purine 6-(3-Bromo-benzo[c]isothiazol-5-ylmethylsulfanyl)-9-butyl-9H-purine and 6-(3-Bromo-benzo[c]isothiazol-5-ylmethylsulfanyl)-9-butyl-9H-purine.

14. A pharmaceutical composition comprising:

at least one thioinosine compound according to claim 1 as an active ingredient and an auxiliary material.

15. A method of alleviating pain in a mammal, said method comprising administering to said mammal an effective pain alleviating amount of a compound according to claim 1.

16. The method of claim 15, wherein said pain is chronic or neuropathic pain.

17. The method of claim 15, wherein said pain is acute.

\* \* \* \* \*